(12) United States Patent
Sun et al.

(10) Patent No.: US 8,367,823 B2
(45) Date of Patent: Feb. 5, 2013

(54) COLORANTS BASED N-HALAMINES COMPOSITIONS AND METHOD OF MAKING AND USING

(75) Inventors: Yuyu Sun, Sioux Falls, SD (US); Jie Luo, Sioux Falls, SD (US)

(73) Assignee: Board of Regents, The University of Texas System, Austin, TX (US)

( * ) Notice: Subject to any disclaimer, the term of this patent is extended or adjusted under 35 U.S.C. 154(b) by 739 days.

(21) Appl. No.: 12/233,925

(22) Filed: Sep. 19, 2008

(65) Prior Publication Data

US 2009/0074825 A1 Mar. 19, 2009

Related U.S. Application Data

(60) Provisional application No. 60/973,647, filed on Sep. 19, 2007.

(51) Int. Cl.
| | |
|---|---|
| C07D 251/00 | (2006.01) |
| C07D 251/12 | (2006.01) |
| C07D 251/18 | (2006.01) |
| C07D 251/40 | (2006.01) |
| C07D 251/50 | (2006.01) |
| A01N 25/00 | (2006.01) |
| A01N 43/66 | (2006.01) |

(52) U.S. Cl. ........ 544/199; 544/180; 544/187; 544/194; 544/208; 424/405; 514/246; 514/612

(58) Field of Classification Search .................... 544/199
See application file for complete search history.

(56) References Cited

U.S. PATENT DOCUMENTS

| 3,285,928 A | 11/1966 | Gubitz |
| 3,488,701 A | 1/1970 | Herbes et al. |
| 3,876,657 A | 4/1975 | Aelony et al. |
| 3,971,757 A | 7/1976 | Rasberger |
| 3,975,462 A | 8/1976 | Murayama et al. |
| 4,091,223 A | 5/1978 | Zussman et al. |
| 4,241,208 A | 12/1980 | Murayama et al. |
| 4,785,055 A | 11/1988 | Dexter et al. |
| 4,931,562 A | 6/1990 | Akabane et al. |
| 5,057,562 A | 10/1991 | Reinert |
| 5,459,145 A | 10/1995 | Saccomano et al. |
| 5,490,983 A | 2/1996 | Worley et al. |

(Continued)

FOREIGN PATENT DOCUMENTS

| EP | 02 40 370 A | 10/1987 |
| GB | 1211521 A | 11/1970 |

(Continued)

OTHER PUBLICATIONS

Nishimoto, et al., "Radiation-induced structural changes in poly (propylene-ran-ethylene) film: effect of antioxidant 2,2,6,6-tetramethylpiperidine derivatives," Radiat. Phys. Chem. (1992), 39(5):413-419.

(Continued)

*Primary Examiner* — Kortney L Klinkel
(74) *Attorney, Agent, or Firm* — Chainey P. Singleton; Edwin S. Flores; Chalker Flores, LLP

(57) ABSTRACT

The present invention includes methods, articles, compositions and colorant dyes and pigments that include biocidal N-halamine dye composition having two or more heterocyclic ring structures attached to one or more N-halamine groups, wherein one or more halogens associate with the one or more one or more N-halamine groups to affect biocidal activity.

6 Claims, 12 Drawing Sheets

12A

12B

U.S. PATENT DOCUMENTS

| | | | |
|---|---|---|---|
| 5,580,872 | A | 12/1996 | Chu et al. |
| 5,670,064 | A | 9/1997 | Worley et al. |
| 5,670,646 | A | 9/1997 | Worley et al. |
| 5,705,545 | A | 1/1998 | Avar et al. |
| 5,714,127 | A | 2/1998 | DeWitt et al. |
| 5,817,806 | A | 10/1998 | Rossi |
| 5,882,357 | A | 3/1999 | Sun et al. |
| 5,889,130 | A | 3/1999 | Worley et al. |
| 5,902,818 | A | 5/1999 | Worley et al. |
| 6,020,491 | A | 2/2000 | Wonley et al. |
| 6,077,319 | A | 6/2000 | Sun et al. |
| 6,162,452 | A | 12/2000 | Worley et al. |
| 6,241,783 | B1 | 6/2001 | Sun et al. |
| 6,294,185 | B1 | 9/2001 | Worley et al. |
| 6,409,941 | B1 | 6/2002 | Galbo et al. |
| 6,482,756 | B2 | 11/2002 | Li |
| 6,576,154 | B1 | 6/2003 | Li |
| 6,585,989 | B2 | 7/2003 | Herbst et al. |
| 6,670,412 | B1 | 12/2003 | Erderly et al. |
| 6,762,225 | B2 | 7/2004 | Malik et al. |
| 6,768,009 | B1 | 7/2004 | Sun et al. |
| 6,770,287 | B1 | 8/2004 | Sun et al. |
| 6,878,761 | B2 | 4/2005 | Gugumus |
| 6,969,769 | B2 | 11/2005 | Worley et al. |
| 7,084,208 | B2 | 8/2006 | Sun et al. |
| 7,335,373 | B2 | 2/2008 | Worley et al. |
| 7,541,398 | B2 | 6/2009 | Sun et al. |
| 2002/0123281 | A1 | 9/2002 | Wu |
| 2003/0056297 | A1 | 3/2003 | Sun |
| 2003/0064645 | A1 | 4/2003 | Worley et al. |
| 2003/0143187 | A1 | 7/2003 | Worley et al. |
| 2003/0216581 | A1 | 11/2003 | Sun et al. |
| 2004/0063831 | A1 | 4/2004 | Sheppard et al. |
| 2004/0086480 | A1 | 5/2004 | Worley et al. |
| 2004/0121681 | A1 | 6/2004 | Quincy et al. |
| 2004/0127667 | A1 | 7/2004 | Worley et al. |
| 2004/0191315 | A1 | 9/2004 | Slattery et al. |
| 2004/0265564 | A1 | 12/2004 | Fischer et al. |
| 2004/0265565 | A1 | 12/2004 | Fischer et al. |
| 2004/0266918 | A1* | 12/2004 | Balliello et al. ............... 524/35 |
| 2005/0186173 | A1 | 8/2005 | Worley et al. |
| 2006/0148940 | A1 | 7/2006 | Sun et al. |
| 2007/0086976 | A1 | 4/2007 | Sun et al. |
| 2007/0092724 | A1 | 4/2007 | Li et al. |

FOREIGN PATENT DOCUMENTS

| | | | |
|---|---|---|---|
| WO | 96 08 949 | A | 3/1996 |
| WO | 01/07550 | A1 | 2/2001 |
| WO | 01/72715 | A2 | 10/2001 |
| WO | 02/06579 | A2 | 1/2002 |
| WO | 02/30477 | A1 | 4/2002 |
| WO | 2005/058814 | A2 | 6/2005 |
| WO | 2006/074455 | A2 | 7/2006 |
| WO | 2007/126775 | A2 | 11/2007 |

OTHER PUBLICATIONS

Aggarwal, P., et al., "Development of an infection-resistant bifunctionalized Dacron biomateria," J Biomed Mater Res (2005), 75A:224-231.

Albert, M., et al., "Structure-Activity Relationships of Oligoguanidines-Influence of Counterion, Diamine, and Average Molecular Weight on Biocidal Activies," Biomacromolecules, (2003), 4:1811-1817.

Amornsakchai, T., et al. ,, "Surface modification of low density polyethylene using accelerated decomposition of potassium persulfate and ceric ion induced acrylamide grafting." J Mater Sci Lett (2002), 21:1035-1038.

Appendini, P., et al., "Review of antimicrobial food packaging," Innov. Food Sci. Emerg. Tech. (2002), 3:113-126.

Barker, J., et al., Effects of cleaning and disinfection in reducing the spread of Norovirus contamination via environmental surfaces, J Hosp Infect (2004), 58:42-49.

Binder, S., et al., "Emerging Infectious Diseases: Public Health Issues for the 21st Century," Science (1999), 284:1311-1313.

Braun, M., et al., "Antimicrobial Polymers Containing Melamine Derivatives. I. Preparation and Characterization of Chloromelamine-Based Cellulose," Polym. Sci., Part A: Polym. Chem. (2004), 42:3818-3827.

Cen, L., et al., "Antibacterial activity of cloth functionalized with Nalkylated poly(4-vinylpyridine)," J Biomed Mater Res (2004), 71A:70-80.

Chen, C. Z., et al., "Quaternary Ammonium Functionalized Poly(propylene imine) Dendrimers as Effective Antimicrobials: Structure-Activity Studies," Biomacromolecules, (2000), 1:473-480.

Chen, Z., et al., N-Chloro-Hindered Amines as Multifunctional Polymer Additives, Macromolecules (2005), 38:8116-8119.

Depaola, L.G., et al., "A review of the science regarding dental unit waterlines." J Am Dent Assoc (2002),133:1199-1206.

Dhamodharan, R., et al., "Investigation of the mercat reaction as a tool for the introduction of nitrogen surface functionality on linear low-density polyethylene (LLDPE) and polypropylene (PP)." Langmuir (2001),17:3368-3374.

Eknoian, M. W., et al., "Monomeric and Polymeric N-Halamine Disinfectants," Ind. Eng. Chem. Res. (1998), 37:2873-2877.

Eknoian, M. W., et al., "Novel Antimicrobial N-halamine polymer coatings generated by emulsion polymerization," Polymer (1999), 40:1367-1371.

Gorman, S.P., et al., "The concomitant development of poly(vinyl chloride)-related biofilm and antimicrobial resistance in relation to ventilator-associated pneumonia." Biomaterials (2001),22:2741-2747.

Hall-Stoodley, L., et al., "Bacterial biofilms: from the natural environment to infectious diseases." Nature Rev Microbiol (2004),2:95-108.

Jansson, A., et al., "Degradation of post-consumer polypropylene materials exposed to simulated recycling—mechanical properties," Polym. Degrad. Stab. (2003), 82:37-46.

Kruczala, K., et al., "Thermal Aging of Heterophasic Propylene-Ethylene Copolymers: Morphological Aspects Based on ESR, FTIR, and DSC," Macromolecules (2003), 36:1899-1908.

Kruczala, K., et al., "Thermal Aging of Heterophasic Propylene-Ethylene Copolymers: Spatial and Temporal Aspects of Degradation Based on ESR, ESR Imaging, and FTIR," Macromolecules (2003), 36:1909-1919.

Larson, M. A., et al., "Inactivation of *Bacillus subtilis* spores with ozone and monochloramine," Water Research (2003), 37:833-844.

Lee, H. J., et al., "Antibacterial effect of nanosized silver colloidal solution on textile fabrics," J Mater Sci (2003), 38:2199-2204.

Lee, S. B., et al., "Permanent, Nonleaching Antibacterial Surfaces. 1. Synthesis by Atom Transfer Radical Polymerization," Biomacromolecules, (2004), 5:877-882.

Lin, J., et al., "Antimicrobial Treatment of Nylon," J Appl Polym Sci (2001), 81:943-947.

Lin, J., et al., "Infrared characterization of biocidal nylon." Polymer (2001), 42:7903-7906.

Linger J.B., et al., "Evaluation of a hydrogen peroxide disinfectant for dental unit waterlines." J Am Dent Assoc (2001),132:1287-1291.

Luo J., et al., "Acyclic N-halamine-based fibrous materials: preparation, characterization, and biocidal functions." J Polym Sci: Part A Polym Chem (2006),44:3588-3600.

Mills S.E., "The dental unit waterline controversy: defusing the myths, defining the solutions." J Am Dent Assoc (2000),131:1427-1441.

Motyakin, M. V., et al., "Spectral Profiling by 1D and 2D Electron Spin Resonance Imaging: Nitroxide Radicals in UV and Thermal Degradation of Poly(acrylonitrile-butadiene-styrene) Containing a Hindered Amine Stabilizer," Macromolecules (2001), 34:2854-2864.

Motyakin, M. V., et al., "Electron Spin Resonance Imaging and ATR-FTIR Study of Poly(acrylonitrile-butadiene-styrene) Containing a Hindered Amine Stabilizer and Thermally Treated at 353 K," Macromolecules (2002), 35:3984-3992.

Muzzarelli, R. A. A., et al., "Fungistatic Activity of Modified Chitosans against *Saprolegnia parasitica*," Biomacromolecules, (2001); 2:165-169.

Neely, A. N., et al. "Survival of *Enterococci* and *Staphylococci* on Hospital Fabrics and Plastic," J Clin Microbiol (2000), 38:724-726.

Neely, A. N., et al., "Survival of Some Medically Important Fungi on Hospital Fabrics and Plastics," J Clin Microbiol (2001), 39:3360-3361.

Ozcan M., et al., "The effect of disinfectant agents in eliminating the contamination of dental unit water." J Oral Rehabili (2003),30:290-294.

Qian, L., et al., "Durable and Regenerable Antimicrobial Textiles: Improving Efficacy and Durability of Biocidal Functions," J Appl Polym Sci (2004), 91:2588-2593.

Rabea, E. I., et al., "Chitosan as Antimicrobial Agent: Applications and Mode of Action," Biomacromolecules, (2003), 4:1457-1465.

Ramage G., et al., "Formation of Propionibacterium acnes biofilms on orthopaedic biomaterials and their susceptibility to antimicrobials." Biomaterials (2003),24:3221-3227.

Roberts H.W., et al., "Dental unit waterline antimicrobial agent: effect on dentin bond strength." J Am Dent Assoc (2000),131:179-183.

Setnescu, R., et al., "Chemiluminescence study on the oxidation of several polyolefins- I. Thermal-induced degradation of additive-free polyolefins," Polym. Degrad. Stab. (1998), 60:377-383.

Sun, G., et al., "Durable and Regenerable Antibacterial Finishing of Fabrics with a New Hydantoin Derivative," Ind Eng Chem Res (2001), 40:1016-1021.

Sun, G., et al., National Center Annual Report, NTC Project C02-CD06 (Nov. 2002).

Sun, Y., et al., "Novel Refreshable N-Halamine Polymeric Biocides Containing Imidazolidin-4-one Derivatives," J Polym Sci Part A Polym Chem (2001), 39:3073-3084.

Sun, Y., et al., "Durable and Regenerable Antimicrobial Textile Materials Prepared by a Continuous Grafting Process," J Appl Polym Sci (2002), 84:1592-1599.

Sun, Y., et al., "Novel Refreshable N-Halamine Polymeric Biocides: N-Chlorination of Aromatic Polyamides," Ind Eng Chem Res (2004), 43:5015-5020.

Tao G., et al., "Surface functionalized polypropylene: Synthesis, characterization, and adhesion properties." Macromolecules (2001),34:7672-7679.

Tennen, R., et al., "Mechanisms of killing of spores of *Bacillus subtilis* by iodine, glutaraldehyde and nitrous acid," J Appl Microbiol (2000), 89:330-338.

Tew, G. N., et al., "De novo design of biomimetic antimicrobial polymers," Proc. Natl. Acad. Sci. USA. (2002), 99:5110-5114.

Tiller, J. C., et al., "Designing Surfaces that Kill Bacteria on Contact," Proc. Natl. Acad. Sci. USA. (2001), 98:5981-5985.

Walker J.T., et al., "Microbiological evaluation of a range of disinfectant products to control mixed-species biofilm contamination in a laboratory model of a dental unit water system." Appl Environ Microbiol (2003),69:3327-3332.

Yorganci K., et al., "Activity of antibacterial impregnated central venous catheters against *Klebsiella pneumoniae*." Intensive Care Med (2002),28:438-442.

International Search Report and Written Opinion for PCT/US2008/076687 dated Apr. 3, 2009.

International Search Report and Written Opinion for PCT/US2007/007506 dated Jul. 25, 2008.

Hahn, K., et al., "Chlorination of Substituted Polyacrylamides," Die Angewandte Makromolekulare Chemie (1976), 50:53-65.

International Search Report for PCT/US2001/09071, dated Jul. 18, 2002.

International Search Report for PCT/US2006/00849, dated Jul. 18, 2002.

Written Opinion for PCT/US2006/00849, dated Jul. 30, 2007.

Sun, Y., et al., "Synthesis, Characterization, and Antibacterial Activities of Novel N-Halamine Polymer Beads Prepared by Suspension Copolymerization," Macromolecules (2002), 35:8909-8912.

Sun, Y., et al., "Novel Refreshable N-Halamine Polymeric Biocides: Grafting Hydantoin-Containing Monomers onto High Performance Fibers by a Continuous Process," J. Appl. Polym. Sci. (2003), 88:1032-1039.

* cited by examiner

2R

2S

2T

2U

2V

12A

12B

16DD

COLORANTS BASED N-HALAMINES COMPOSITIONS AND METHOD OF MAKING AND USING

CROSS-REFERENCE TO RELATED APPLICATIONS

This application claims priority to U.S. Provisional Application Ser. No. 60/973,647, filed Sep. 19, 2007, the contents of which is incorporated by reference herein in its entirety.

This application is a related to U.S. Provisional Patent Application Ser. No. 60/707,331, filed Aug. 11, 2005, and U.S. patent application Ser. No. 11/324,616, filed Jan. 3, 2006, which claims priority to U.S. Provisional Patent Application Ser. No. 60/640,985, filed Jan. 3, 2005, the contents of each of which are incorporated by reference herein in their entireties. This application is also related to U.S. patent application Ser. No. 11/389,968, filed Mar. 27, 2006 and U.S. Provisional patent application Ser. No. 11/502,892, filed Aug. 11, 2006, the contents of each of which are incorporated by reference herein in their entireties.

TECHNICAL FIELD OF THE INVENTION

The present invention relates in general to the field of multifunctional additives of materials, and more particularly, to the colorants-based N-halamines as additives and materials to provide rechargeable biocial activity of a colored composition.

BACKGROUND OF THE INVENTION

Without limiting the scope of the invention, its background is described in connection with colorants-based N-halamines additive compounds that act as multifunctional materials, as an example.

Currently many different articles include a pigment or organic dye in order to add color. The colorant (i.e., pigment or organic dye) may be added to the surface or dispersed into other materials, e.g., plastics, solutions, fibers and so forth. Colorants have been used in various materials to merely add color to the article and provides no secondary benefits to the article. Although, the article may now be colored, it is still susceptible to contamination.

Contamination may take the form of microorganisms such as pathogenic bacteria, molds, fungi and viruses. These are of great concern in many areas including the medical industry, the food and restaurant industries and consumer products. In addition, these contaminations provide the potential for the spread of infections over a variety of environments. Survival of microorganisms on various materials and transfer of these microorganisms between materials, animals and humans has been demonstrated, and it is widely accepted that microorganism-contaminated materials can be elements in cross-infections and transmission of diseases caused by microorganisms. Complicating this problem is the microorganism's strong abilities to survive on ordinary materials, e.g., 90 days or longer.

Another common problem includes the development of these microorganisms into biofilms which are an accumulation of microorganisms (e.g., bacteria, fungi, and/or protozoa, with associated bacteriophages and other viruses) embedded in a polysaccharide matrix. Biofilms can adhere to solid biologic or non-biologic surface and allow the growth and proliferation of contaminants and make the cleaning and removal of pathogenic bacteria, molds, fungi and viruses extremely difficult.

Biofilms are remarkably difficult to treat with antimicrobials. In some cases the antimicrobials compositions may be readily inactivated or fail to penetrate into the biofilm. Furthermore, the microorganisms distributed throughout the biofilm may be geographically different distributions and the same species microorganisms may have different characteristic depending on the geographical location in the biofilm. For example, microorganisms within the biofilm may have an increased (e.g., up to 1000-fold higher) resistance to antimicrobial compounds, even though these same microorganisms are sensitive to these agents if grown under planktonic conditions. Furthermore, microorganisms express new, and sometimes more virulent phenotypes when grown within a biofilm. Such phenotypes may not have been detected in the past because the organisms were grown on rich nutrient media under planktonic conditions. The growth conditions are quite different particularly in the depths of biofilms, where nutrients and oxygen are usually limited, and waste products from neighbors can be toxic. In short, microorganisms found at the bottom of the biofilm look and act different from microorganisms located at the surface.

Biofilms represent a serious problem in environmental, medical and industrial fields as they increase the opportunity for gene transfer between/among microorganisms allowing microorganisms resistant to antimicrobials or chemical biocides to transfer the genes for resistance to neighboring susceptible microorganisms. Gene transfer can convert a previous avirulent commensal organism into a highly virulent pathogen. Certain species of microorganisms communicate with each other within the biofilm. As their density increases, the organisms secrete low molecular weight molecules that signal when the population has reached a critical threshold, e.g., quorum sensing, is responsible for the expression of virulence factors.

Microorganisms embedded within biofilms are resistant to both immunological and non-specific defense mechanisms of the body. Contact with a solid surface triggers the expression of a panel of bacterial enzymes, which catalyze the formation of sticky polysaccharides that promote colonization and protection. The structure of biofilms is such that immune responses may be directed only at those antigens found on the outer surface of the biofilm, and antibodies and other serum or salivary proteins often fail to penetrate into the biofilm. In addition, phagocytes are unable to effectively engulf a bacterium growing within a complex polysaccharide matrix attached to a solid surface. This causes the phagocyte to release large amounts of pro-inflammatory enzymes and cytokines, leading to inflammation and destruction of nearby tissues. Because biofilm formation is triggered by the survival and adherence of microbes onto different materials, the introduction of biocidal functions into the target materials can be an effective method to inactivate the microbes and thus control biofilms.

In addition to the medical and healthcare fields, the food and restaurant industries, as well as in consumer are increasingly concerned with microbial contamination, e.g., food contact between contaminated articles. Multiple outbreaks of food borne bacterium such as *E. coli*, have made people increasingly conscious of methods to control the spread of such bacterium. Food contact materials such as cutting boards, sponges, towels and the like have long been suspected to be vectors for the spread of food borne microorganisms. Therefore, the induction of biocidal properties should be an effective feature of healthcare and hygienic-use applications.

The foregoing problems have been recognized for many years and while numerous solutions have been proposed, none of them adequately address all of the problems in a single device, e.g., effectiveness against many forms of bacteria, toxicity, while providing stability and rechargeability.

SUMMARY OF THE INVENTION

The present inventor recognized that what is needed is a method for converting pigment and organic dye normally used to add color to an article into biocidal active compositions. The present inventors recognized that many pigments and organic dyes used to add color have functional groups that may be halogenated to from N-halamine biocidal dye compounds.

The present invention provides a biocidal N-halamine dye composition having two or more heterocyclic ring structures attached to one or more N-halamine groups. One or more halogens associate with the one or more one or more N-halamine groups to affect biocidal activity.

The present invention provides a biocidal N-halamine dye composition where the N-halamine biocidal composition is integrated into a bead, a film, a tube, a sheet, a thread, a suture, a gauze, a bandage, an adhesive bandage, a vessel, a container, a cistern, a filter, a membrane, a coating, a paint, a solution, a polymer and combinations thereof.

The present invention provides a biocidal N-halamine dye composition where the N-halamine biocidal composition comprises formula illustrated in FIG. 1, 2, 3, 4, 5, 6, 7, 8, 9, 10, 11, 12, 13, 14, 15 or 16 wherein X, $X_1$, $X_2$, $X_3$ and $X_4$ are individually a hydrogen, a halogen, an alkyl, an alkylene, an amino, an alkynyl, an alkoxy; R1 to R10 are independently hydrogens, halogens, one or more $C_1$ to $C_{40}$ alkyl, $C_1$ to $C_{40}$ alkylene, $C_1$ to $C_{40}$ alkenyl, $C_1$ to $C_{40}$ alkynyl, $C_1$ to $C_{40}$ aryl, $C_1$ to $C_{40}$ alkoxy, C1 to to $C_{40}$ alkylcarbonyl, $C_1$ to $C_{40}$ alkylcarboxyl, $C_1$ to $C_{40}$ amido, C1 to $C_{40}$ carboxyl, or combinations thereof.

In addition the present invention also provides a method of halogenating a biocidal N-halamine dye article by providing a N-halamine dye article comprising one or more N-halamine biocidal compounds comprising two or more heterocyclic ring structures attached to one or more N-halamine groups, wherein one or more halogens associate with the one or more one or more N-halamine groups to affect biocidal activity and exposing the N-halamine dye article to a halogen source. The N-halamine biocidal dye composition may have the structure seen in FIGS. 1-16. The one or more N-halamine biocidal compounds may be added by solution blending, mechanical mixing, painting, coating, laminating, thermal mixing and combinations thereof. In addition, the N-halamine biocidal dye composition may by the step of recharging the one or more N-halamine groups by exposing to a halogen source.

The present invention also provides a biofilm resistant surface. The surface includes one or more N-halamine biocidal compounds immobilized to the surface to form a biofilm resistant surface. The one or more N-halamine biocidal compounds include two or more heterocyclic ring structures attached to one or more N-halamine groups. In addition, one or more halogens are associated with the one or more one or more N-halamine groups to affect biocidal activity.

The surface comprises at least a portion of a fabric, a cloth, a material, a garment, synthetic fabric or a polymer and the one or more N-halamine biocidal compounds is integrated into a bead, a film, a tube, a sheet, a thread, a suture, a gauze, a bandage, an adhesive bandage, a vessel, a container, a cistern, a filter, a membrane, a coating, a paint, a solution, a polymer and combinations thereof.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
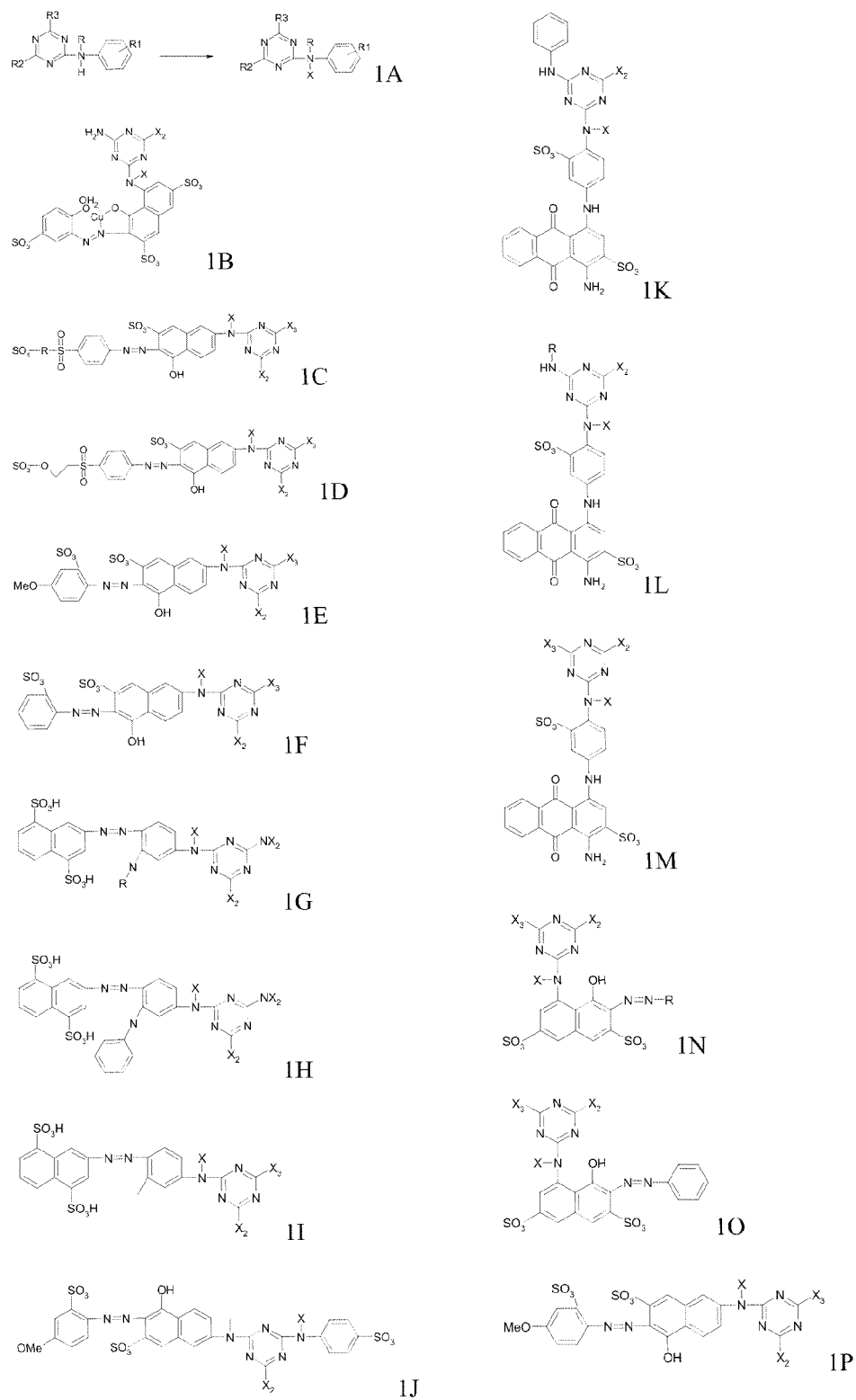
FIGS. 1A-1Z are images of the structure of colorants-based N-halamine compounds of the present invention.
Figure 1:
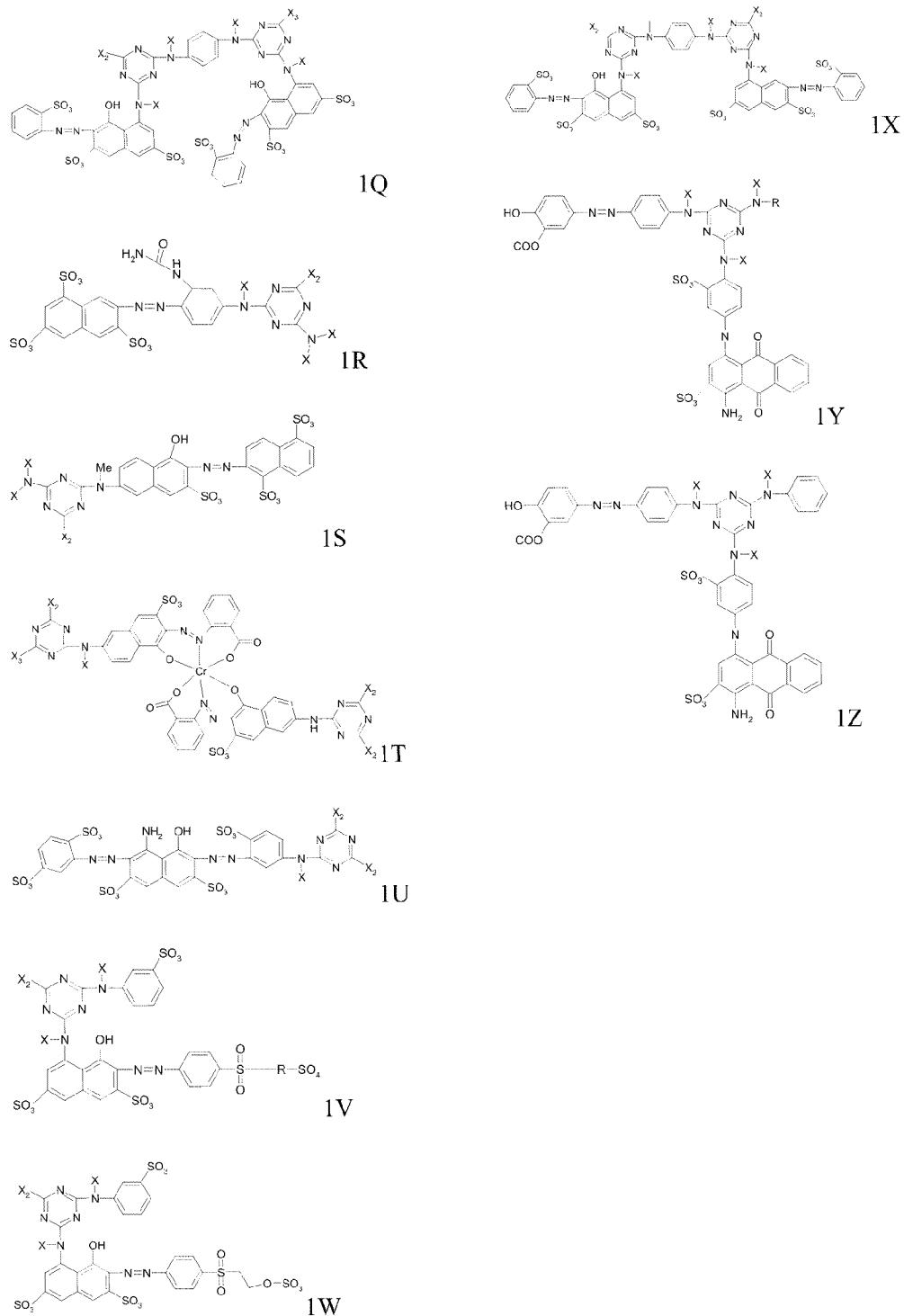

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The terms "antimicrobial compound," "antimicrobial," "microbicidal," "biocide," "biocidal" and "halogenated amide antimicrobial" are used interchangeably herein and refer to halogenated amides that function as biocides to kill at least some types of microorganisms, or to inhibit the growth or reproduction of at least some types of microorganisms (i.e., compounds which inhibit the growth of, or kills, microorganisms such as bacteria, molds, slimes, fungi, etc.).

As used herein, the term "alkyl" denotes branched or unbranched hydrocarbon chains, preferably having about 1 to about 10 carbons, such as, methyl, ethyl, n-propyl, iso-propyl, n-butyl, sec-butyl, iso-butyl, tert-butyl, octa-decyl and 2-methylpentyl. These groups can be optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, alkyl, alkenyl, nitro, amino, alkoxyl, amido, and the like to form alkyl groups such as trifluoro methyl, 3-hydroxyhexyl, 2-carboxypropyl, 2-fluoroethyl, carboxymethyl, cyanobutyl and the like.

The term "alkylene" refers to a divalent alkyl group as defined above, such as methylene ($-CH_2-$), propylene ($-CH_2CH_2CH_2-$), chloroethylene ($-CHClCH_2-$), 2-thiobutene ($-CH_2CH(SH)CH_2CH_2$), 1-bromo-3-hydroxyl-4-methylpentene ($-CHBrCH_2CH(OH)CH(CH_3)CH_2-$), and the like.

As used herein, the term "alkenyl" denotes branched or unbranched hydrocarbon chains containing one or more carbon-carbon double bonds.

The term "alkynyl" refers to branched or unbranched hydrocarbon chains containing one or more carbon-carbon triple bonds.

As used herein, the term "aryl" denotes a chain of carbon atoms which form at least one aromatic ring having between about 4-50 carbon atoms, such as phenyl, naphthyl, triazine, naphthalene, Anthracene, Anthraquinone and the like, and which may be substituted with one or more functional groups which are attached commonly to such chains, such as hydroxyl, bromo, fluoro, chloro, iodo, mercapto or thio, cyano, cyanoamido, alkylthio, heterocycle, aryl, heteroaryl, carboxyl, carbalkoyl, alkyl, alkenyl, nitro, amino, alkoxyl, amido, and the like to form aryl groups such as biphenyl, iodobiphenyl, methoxybiphenyl, anthryl, bromophenyl, iodophenyl, chlorophenyl, hydroxyphenyl, methoxyphenyl, formylphenyl, acetylphenyl, trifluoromethylthiophenyl, trifluoromethoxyphenyl, alkylthiophenyl, trialkylammoniumphenyl, amidophenyl, thiazolylphenyl, oxazolylphenyl, imidazolylphenyl, imidazolylmethylphenyl, and the like.

The term "alkoxy" denotes $-OR-$, wherein R is alkyl. The term "alkylcarbonyl" denote an alkyl group as defined above substituted with a C(O) group, for example, $CH_3C(O)-$, $CH_3CH_2C(O)-$, etc. As used herein, the term "alkylcarboxyl" denote an alkyl group as defined above substituted with a $-C(O)O$ group, for example, $CH_3C(O)O-$, $CH_3CH_2C(O)O-$, etc. As used herein, the term "amido" denotes an amide linkage: $-C(O)NHR$ (wherein R is hydrogen or alkyl). The term "amino" denotes an amine linkage: $-NR-$, wherein R is hydrogen or alkyl. The term "carbocycle" means a cyclic hydrocarbon chain having about 4 to about 8 ring carbons such as cyclopentyl, cylcohexyl, etc. These groups can be optionally substituted with one or more functional groups as defined under "alkyl" above.

As used herein, the term "carboxyl" denotes $-C(O)O-$, and the term "carbonyl" denotes $-C(O)-$. The term "cycloalkyl" signifies a saturated, cyclic hydrocarbon group with 3-8, i.e. cyclopropyl, cyclobutyl, cyclopentyl and cyclohexyl and the like.

As used herein, the terms "N-halamine dye," "Heterocyclic N-halamine dye," "cyclic N-halamine dye" and "N-halamine pigments" denotes a class of chemicals that contain a halogen bound to a nitrogen atom, where the nitrogen is a member of a ring, along with carbon atoms or in communication (e.g., bound to the ring) with the ring. When bound to the nitrogen, the halogen is in a stable form and retains the ability to interact with targets on the surfaces of bacteria and other microbes. The presence of the halogen renders it biocidal. For example, heterocyclic, monocyclic compounds having 4 to 8 membered ring, wherein at least 3 members of the ring are carbon, and from 1 to 3 members of the ring are nitrogen heteroatom, and from 0 to 1 member of the ring is oxygen heteroatom. Additionally, there may be from 0 to 3 carbon members comprise a carbonyl group, and wherein at least 1 to 3 nitrogen atoms are substituted with a hydroxyalkyl group, such as $-CH_2OH$, or an alkoxyalkyl group, such as $-CH_2OCH_3$. In addition, the ring members can be further substituted with alkyl groups, such as methyl, ethyl, etc.

The term "halogen" includes chlorine, fluorine, bromine, iodine and mixtures thereof. As used throughout the specification halogens may be used interchangeably. Although specific figures are represented with a specific halogen, the skilled artisan will clearly understand that the halogen may be substituted with other halogens. As used herein, the specific halogen or general halogen group X may be chlorine, fluorine, bromine, or iodine and not intended to limit the specific molecule to only a single halogen. The general halogen group is denoted herein by X and in some instances $X_2$ which denotes 2 halogens that may be independently a chlorine, a fluorine, a bromine, or an iodine.

The term "heteroaryl" refers to an aromatic monocyclic or bicyclic radical having 5 to 10, preferably 5 to 6 ring atoms, containing one to three heteroatoms, e.g. independently selected from nitrogen, oxygen or sulfur. Examples of heteroaryl groups are thiophenyl, isoxazolyl, thiazolyl, piperidinyl, pyridinyl, pyrrolyl, imidazolyl, tetrazolyl, pyridinyl, isoxazolyl or thiazolyl. Optionally, the heteroaryl group can be mono-substituted, di-substituted or tri-substituted, independently, with phenyl, alkyl, alkylcarbonyl, alkoxycarbonyl, hydroxy, amino, alkylamino, dialkylamino, carboxy, alkoxycarbonylalkyl, preferably alkyl. In addition, the compound may have one or more heteroaryl or Polycyclics attached to the base structure.

As used herein the term "Polycyclics" denotes organic compounds that are molecules containing two or more simple aromatic rings fused together by sharing two neighboring carbon atoms. Examples are naphthalene, anthracene and phenanthrene. In addition, the present invention may include one or more substituted aromatics. Many chemical compounds contain simple aromatic rings in their structure. For example, pyrrole, or pyrrol, is a heterocyclic aromatic organic compound having five-membered ring with the formula $C_4H_4NH$. Pyridine is a chemical compound with the formula $C_5H_5NH$ and in addition substituted derivatives may also called pyrroles. In addition some of the molecules of the present invention may have one or more imide functional groups that include two carbonyl groups bound to a primary amine or ammonia, for example, phthalimide. They may be either simple aromatic rings or non-aromatic rings. Some examples are pyridine, pyrimidine, triazine, dioxane, pyridine, imidazole, pyrazole, oxazole, thiophene, and their benzannulated analogs (e.g., benzimidazole).

The term "heterocycle" means a straight chain or ring system that may contain from zero to four heteroatoms selected from N, O and S, wherein the nitrogen and sulfur atoms are optionally oxidized and the nitrogen atom(s) may be optionally quaternized. These groups can be themselves be optionally substituted with one or more functional groups as defined above.

As used herein, the terms, "polymer" and "copolymer" are at times used interchangeably to mean a cyclic amine or N-halamine unit joined by a linkage to a second cyclic amine or N-halamine unit is not meant to be limiting as to the number of cyclic amine or N-halamine units in a polymer, e.g., two or more cyclic amine or N-halamine units, and the number of units in any given polymer can vary according to the use intended for the polymer. Other polymers include flexible PVC, polyurethanes, polyolefins, thermoplastic polyolefins, thermoplastic elastomers, rubber, silicones, polyester; however, the skilled artisan will recognize other polymers may be used. The polymer may be a random copolymer contains a random arrangement of the multiple monomers. The polymer may be a block copolymer contains blocks of monomers of the same type. The polymer may also be a graft copolymer contains a main chain polymer consisting of one type of monomer with branches made up of other monomers. For example, the polymer can comprise 2, 3, 4, 5, 6, 7, 8, 9, 10, 20, 25, 30, 40, 50, 75, 100, 150, 200, 250, 500, 1000 units, or more.

The present invention provides a method of making a rechargeable antimicrobial and biofilm-controlling material by synthesizing one or more N-halamine biocidal dye compounds and adding one or more N-halamine biocidal dye compounds to a target material. The target material is used directly, or processed into the desired articles, coatings, paints, medical devices and so forth.

The present invention includes methods, articles, compositions and colorant dyes and pigments that include biocidal N-halamine dye composition having two or more heterocyclic ring structures attached to one or more N-halamine groups, wherein one or more halogens associate with the one or more one or more N-halamine groups to affect biocidal activity.

The present invention includes N-halamine biocidal dye compounds having individually a Hydrogen, a halogen, optionally one or more R groups being independently hydrogens, halogens, aryls, one or more $C_1$ to $C_{40}$ alkyl, $C_1$ to $C_{40}$ alkylene, $C_1$ to $C_{40}$ alkenyl, $C_1$ to $C_{40}$ alkynyl, $C_1$ to $C_{40}$ aryl, $C_1$ to $C_{30}$ alkoxy, $C_1$ to $C_{40}$ alkylcarbonyl, $C_1$ to $C_{40}$ alkylcarboxyl, $C_1$ to $C_{40}$ amido, $C_1$ to $C_{40}$ carboxyl, or combinations thereof.

Additionally, the N-halamine biocidal dye compound may be in communication with or bonded to, either covalently or ionically, one or more halogens. In addition the presence of halogen may be replenished when concentrations are low doe to activity, diffusion, reactivity, redox reactions through the treatment a hypohalogenic solution, e.g., hypochlorite or hypoborite solution.

Furthermore, biofilm controlling N-halamine biocidal dye compounds which are stable to photo and thermal treatment may be made by mixing an N-halamine biocidal dye compound with a source of halide atoms to form a N-halamine biocidal dye compound and forming a material in the presence of the N-halamine biocidal dye compound.

The N-halamine biocidal dyes compounds may be integrated into a polymer as stabilization agents, polymeric materials, copolymers, additives or the like. The target material may be a polymer in the form of plastics, cellulose, rubbers, fibers, woods, paints, coatings.

FIGS. 1A to 1Z are structures of N-halamine biocidal dye compounds and N-halamine biocidal pigments synthesized from the chlorination or bromination of selected reactive dyes. FIG. 1A is the general reaction schematic wherein a dye or a pigment having a haloamine is exposed to a source of halogens to form a N-halamine biocidal dye or a N-halamine biocidal pigment. The resulting N-halamine biocidal dye compounds may be used for antimicrobial and anti-biofilm applications. The general structure is given in FIG. 1A and includes an amine connected to a triazine, an aromatic ring structure, optionally an R group and a hydrogen that may be replaced by a halogen to form a N-haloamine. The amine may be individually connected to the triazine, the aromatic ring structure, and/or the R group directly or through a connecting molecule or linking compound. Although the triazine structure (i.e., a heterocyclic ring, analogous to the six-membered benzene ring but with three carbons replaced by nitrogens) may be a 1,3,5-triazine, modified and substituted triazine structures are also contemplated with the present invention. For example, the triazine present in FIG. 1A includes substituted groups $R_2$ and $R_3$. The skilled artisan will recognize that these substitutions may take many forms. For example, the $R_1$, $R_2$ and $R_3$ groups may independently be an alkyl group, an alkylene group, an alkenyl group, an alkynyl group, an aryl group, an alkoxy group, an alkylcarbonyl group, an alkylcarboxyl group, an amido group, a carboxyl group or a halogen. Furthermore the R group may be substituted with one or more alkyl groups, alkylene groups, alkenyl groups, alkynyl groups, aryl groups, alkoxy groups, alkylcarbonyl groups, alkylcarboxyl groups, amido groups, carboxyl groups, halogens or hydrogens.

FIGS. 1B-1Z illustrate numerous examples of dye molecules that may be used and converted into biocidal dyes and pigments by the present invention. These compounds can provide potent, durable and rechargeable biocidal functions against bacteria, fungus, yeast, virus and spores. As seen in FIGS. 1A-1Z, the N—X (e.g., X and $X_2$ are halogens) structures are stable N-halamines. The halogen(s) X and/or $X_2$ may be independently chlorine, fluorine, bromine and iodine. When more than one halogen is bonded to the molecule it is not necessary for the halogens to be similar, they may be a mixture of chlorine, fluorine, bromine and iodine at any given location.

Another example includes a halogenated amine attached to an optionally substituted triazine and to two R groups. The R groups may be a hydroxyl, bromo, fluoro, chloro, iodo, mercapto or thio, cyano, cyanoamido, alkylthio, heterocycle, aryl, heteroaryl, carboxyl, carbalkoyl, alkyl, alkenyl, nitro, amino, alkoxyl, amido, and the like to form aryl groups such as biphenyl, iodobiphenyl, methoxybiphenyl, anthryl, bromophenyl, iodophenyl, chlorophenyl, hydroxyphenyl, methoxyphenyl, formylphenyl, acetylphenyl, trifluoromethylthiophenyl, trifluoromethoxyphenyl, alkylthiophenyl, trialkylammoniumphenyl, amidophenyl, thiazolylphenyl, oxazolylphenyl, imidazolylphenyl, imidazolylmethylphenyl, and the like. As seen in FIG. 1 the R groups may be varied to provide numerous structures; in addition, complex multiple fused rings may be included in some structures of the present invention, e.g., FIGS. 1Q, 1T, 1V and 1W-1Z.

The basic formulas illustrated in FIGS. 1A-1Z may be substituted with one or more functional groups at one or more of the R positions, e.g., R, $R^1$, $R^2$, $R^3$ and $R^4$. The skilled artisan will recognize that the R group substitution may take many forms, e.g., the R group may independently be an alkyl group, an alkylene group, an alkenyl group, an alkynyl group, an aryl group, an alkoxy group, an alkylcarbonyl group, an alkylcarboxyl group, an amido group, a carboxyl group or a halogen. Furthermore the R group may be substituted with one or more alkyl groups, alkylene groups, alkenyl groups, alkynyl groups, aryl groups, alkoxy groups, alkylcarbonyl groups, alkylcarboxyl groups, amido groups, carboxyl groups or halogens.

For example, the N-halamine biocidal dye compounds may be substituted individually a Hydrogen, a halogen, one or more $C_1$ to $C_{40}$ alkyl, $C_1$ to $C_{40}$ alkylene, $C_1$ to $C_{40}$ alkenyl, $C_1$ to $C_{40}$ alkynyl, $C_1$ to $C_{40}$ aryl, $C_1$ to $C_{30}$ alkoxy, $C_1$ to $C_{40}$ alkylcarbonyl, $C_1$ to $C_{40}$ alkylcarboxyl, $C_1$ to $C_{40}$ amido, $C_1$ to $C_{40}$ carboxyl, aryls or combinations thereof.

In some instances the N-halamine biocidal dye compounds may include one or more connecting or linking molecules between the nitrogen of the amine and the other groups. For example, in some instances a linker group may be used to connect the amine to the triazine, the aromatic ring structure, and/or the R group. The one or more connecting or linking molecules may be aliphatic or aromatic.

Additionally, the N-halamine biocidal compound may be in communication with or bonded to, either covalently or ionically, one or more halogens. In addition the presence of halogen may be replenished when concentrations are low due to activity, diffusion, reactivity, redox reactions through the treatment a hypohalogenic solution, e.g., hypochlorite or hypoborite solution.

For example, FIG. 1B represents a schematic of a N-halamine biocidal molecule modified pursuant to the present invention which is a modification of the molecule identified by CAS number 6646-12-9; [5-[(4-amino-6-chloro-1,3,5-triazin-2-yl)amino]-4-(hydroxy-κO)-3-[[2-(hydroxy-κO)-5-sulfophenyl]azo-κN1]-2,7-naphthalenedisulfonato(5-)]aqua-Cuprate(3-); Cuprate(3-), [5-[(4-amino-6-chloro-1,3,5-triazin-2-yl)amino]-4-hydroxy-3-[(2-hydroxy-5-sulfophenyl)azo]-2,7-naphthalenedisulfonato(5-)]aqua-, trisodium; 2,7-Naphthalenedisulfonic acid, 5-[(4-amino-6-chloro-1,3,5-triazin-2-yl)amino]-4-hydroxy-3-[(2-hydroxy-5-sulfophenyl)azo]-copper complex; Reactive Violet 4K; Violet 4K. For example, FIGS. 1C, 1D and 1E illustrate schematics of a N-halamine biocidal modified pursuant to the present invention which are modifications of the molecule identified by CAS number 129009-88-7; 7-[(4,6-dichloro-1, 3,5-triazin-2-yl)amino]-4-hydroxy-3-[[4-[[2-(sulfooxy) ethyl]sulfonyl]phenyl]azo]-2-Naphthalenesulfonic acid, disodium salt (9Cl).

For example, FIG. 1F represents a schematic of a molecule modified pursuant to the present invention which is a modification of the molecule identified by CAS number 6522-74-3; 7-[(4,6-dichloro-1,3,5-triazin-2-yl)amino]-4-hydroxy-3-[(2-sulfophenyl)azo]-2-Naphthalenesulfonic acid (9Cl); also known by 1-Naphthol-3-sulfonic acid, 6-[(4,6-dichloro-s-triazin-2-yl)amino]-2-(o-sulfophenylazo)-(6Cl); 2-Naphthalenesulfonic acid, 7-[(4,6-dichloro-s-triazin-2-yl)amino]-4-hydroxy-3-[(o-sulfophenyl)azo]-(7Cl); C.I. Reactive Orange 1 (8CI); BRYreact Brilliant Orange X-GN; Mikacion Brilliant Orange GS; Mikacion Orange GS; Procion Brilliant Orange M-G; Procion Brilliant Orange MX-G; Procion Orange MX-G; Reactive Brilliant Orange X-GN; Reactive Orange 1.

For example, FIGS. 1G and 1H illustrate schematics of N-halamine biocidal molecules modified pursuant to the present invention which are modifications of the molecule identified by CAS number 6539-67-9; 3-[[2-(acetylamino)-4-[(4-amino-6-chloro-1,3,5-triazin-2-yl)amino]phenyl]azo]-1,5-Naphthalenedisulfonic acid (9Cl); also known by 1,5-Naphthalenedisulfonic acid, 3-[[2-acetamido-4-[(4-amino-6-chloro-s-triazin-2-yl)amino]phenyl]azo]-(6Cl); C.I. Reactive Yellow 3 (7Cl,8Cl); Basilen Yellow E 3R; C.I. 13245; Chemictive Yellow RH; Cibacron Yellow FR-A; Cibacron Yellow R-A; Helaktyn Yellow D-GR; Helaktyn Yellow D-GRE; Orbaktiv Yellow T-RA; Ostazin Yellow H-A; Procion Yellow H-A; Procion Yellow HAS; Reactive Yellow 3; Reactive Yellow MR. For example, FIG. 1I represents a schematic of a N-halamine biocidal molecule modified pursuant to the present invention which is a modification of the molecule identified by CAS number 12226-45-8; 3-[[4-[(4,6-dichloro-1,3,5-triazin-2-yl)amino]-2-methylphenyl]azo]-1,5-Naphthalenedisulfonic acid, disodium salt (9Cl); also known by 1,5-Naphthalenedisulfonic acid, 3-[[4-[(4,6-dichloro-s-triazin-2-yl)amino]-o-tolyl]azo]-, disodium salt (7Cl,8Cl); Active Golden Yellow KKh; C.I. Reactive Yellow 4; Mikacion Yellow RS; Procion Yellow 11X-R; Procion Yellow M-R; Procion Yellow MX-R; Procion Yellow RS; Reactive Golden Yellow 2KKh; Reactive Golden Yellow KKh; Reactive Yellow 4; Reactive Yellow X-R; Reactive Yellow X-RG.

FIG. 1J represents a schematic of a N-halamine biocidal molecule modified pursuant to the present invention which is a modification of the molecule identified by CAS number 12237-01-3; 7-[[4-chloro-6-[(4-sulfophenyl)amino]-1,3,5-triazin-2-yl]methylamino]-4-hydroxy-3-[(4-methoxy-2-sulfophenyl)azo]-2-Naphthalenesulfonic acid, trisodium salt (9Cl); also known by C.I. Reactive Red 33 (8Cl); Procion Scarlet H-RN; Reactive Red 33. For example, FIGS. 1K and 1L illustrate schematics of N-halamine biocidal molecules modified pursuant to the present invention which are modifications of the molecule identified by CAS number 12236-82-7; 1-amino-4-[[4-[[4-chloro-6-[[3(or 4)-sulfophenyl]amino]-1,3,5-triazin-2-yl]amino]-3-sulfophenyl]amino]-9,10-dihydro-9,10-dioxo-2-Anthracenesulfonic acid, (9Cl); also known by C.I. Reactive Blue 2 (8Cl); Basilen Blue E 3G; Blue A; C.I. 61211; Cibacron Blue F 3GA; Kayacion Blue A-B; Procion Blue H-B; Reactive Blue 2. For example, FIG. 1M represents a schematic of a N-halamine biocidal molecule modified pursuant to the present invention which is a modification of the molecule identified by CAS number 13324-20-4; 1-amino-4-[[3-[(4,6-dichloro-1,3,5-triazin-2-yl)amino]-4-sulfophenyl]amino]-9,10-dihydro-9,10-dioxo-2-anthracenesulfonic acid, (9Cl); also known by 2-Anthracenesulfonic acid, 1-amino-4-[3-[(4,6-dichloro-s-triazin-2-yl)amino]-4-sulfoanilino]-9,10-dihydro-9,10-dioxo-(8Cl); 2-Anthraquinonesulfonic acid, 1-amino-4-[3-[(4,6-dichloro-s-triazin-2-yl)amino]-4-sulfoanilino]- (6Cl); C.I. 61205; C.I. Reactive Blue 4; Helaktyn Blue FR; Helaktyn Pure Blue F-R; Mikacion Brilliant Blue RS; NSC 364368; Orbaktiv Brilliant Blue M-R; Ostazin Blue S-R; Ostazin Brilliant Blue S-R; Procion Blue 11X-R; Procion Blue MR; Procion Blue MX-R; Procion Brilliant Blue MR; Procion Brilliant Blue MX-R; Procion Brilliant Blue RS; Reactive Blue 4; Reactive Blue MR; Reactive Blue X-BR; Reactive Brilliant Blue X-BR; Sigma Reactive Blue 4.

For example, FIGS. 1N and 1O illustrate schematics of one embodiment of N-halamine biocidal molecules modified pursuant to the present invention which are modifications of the molecule identified by CAS number 17804-49-8; 5-[(4,6-dichloro-1,3,5-triazin-2-yl)amino]-4-hydroxy-3-(phenylazo)-2,7-Naphthalenedisulfonic acid, disodium salt (9Cl); also known by 2,7-Naphthalenedisulfonic acid, 5-[(4,6-dichloro-s-triazin-2-yl)amino]-4-hydroxy-3-(phenylazo)-, disodium salt (7Cl,8Cl); 5-(4,6-Dichloro-s-triazinyl-2-amino)-4-hydroxy-3-(phenylazo)-2,7-naphthalenedisulfonic acid disodium salt; Basilen Red M 5B; Brilliant Red 5SKh; Brilliant Red X 3B; C.I. Reactive Red 2; Chemictive Brilliant Red 5B; Halaktyn Red F 5B; Intracron Red C 5B; Mikacion Brilliant Red 5BS; Orbaktiv Brilliant Red M 5B; Ostazin Brilliant Red S 5B; Ostazin Red S 5B; Procion Brilliant Red 5BS; Procion Brilliant Red M 5B; Procion Brilliant Red MX 5B; Procion Red 5CX; Procion Red 5MX; Procion Red M 5B; Procion Red MX 5B; Reactive Bright Red X 3B; Reactive Brilliant Red (Chinese); Reactive Brilliant Red 5SKh; Reactive Brilliant Red X 3B; Reactive Red 2; Reactive Red 5SKh; Reactive Red B 5A; Reactive Red X 3B; Reactofix Brilliant Red M 5B.

For example, FIG. 1P represents a schematic of a N-halamine biocidal molecule modified pursuant to the present invention which is a modification of the molecule identified by CAS number 25489-36-5; 7-[(4,6-dichloro-1,3, 5-triazin-2-yl)amino]-4-hydroxy-3-[(4-methoxy-2-sulfophenyl)azo]-2-Naphthalenesulfonic acid, disodium salt (9CI); also known by C.I. Reactive Red 8, disodium salt (8CI); C.I. Reactive Red 8; Helaktyn Scarlet FG; Mikacion Scarlet GS; Procion Scarlet GS; Procion Scarlet M-G; Procion Scarlet MX-G; Reactive Red 8. For example, FIG. 1Q represents a schematic of a N-halamine biocidal molecule modified pursuant to the present invention which is a modification of the molecule identified by CAS number 61951-82-4; 2,7-Naphthalenedisulfonic acid, 4,4'-[1,4-phenylenebis[imino(6-chloro-1,3,5-triazine-4,2-diyl)imino]]bis[5-hydroxy-6-[(2-sulfophenyl)azo]- (9CI); also known by 1-Naphthol-3,6-disulfonic acid, 8,8'-[p-phenylenebis[imino (6-chloro-s-triazine-4,2-diyl)imino]]bis[2-(o-sulfophenylazo)-(6CI); Basacid Red NB 510; Basilen Red E-B; Brilliant Red HE 3B; C.I. 292775; C.I. Reactive Red 120; Cibacron Brilliant Red 4G-E; Cibacron Red 4G-E; Cibacron Red 4G-E01; Drimarene Brilliant Red A 4G; Evercion Red H-E 3B; Fastusol Red 53L; Helaktyn Red DE-BN; Intracron Brilliant Red 4G-E; Intracron Brilliant Red E 3B; Kayacion Red E-S 3B; Procion Brilliant Red H-E 3B; Procion Red H-E 3B; Procion Red MX 3B; Reactive Brilliant Red KE 3B; Reactive Red 120; Reactive Red HE 3B; Red A; Taifix Red HE 3BT.

For example, FIG. 1R represents a schematic of a N-halamine biocidal molecule modified pursuant to the present invention which is a modification of the molecule identified by CAS number 70161-14-7; 7-[[2-[(aminocarbonyl)amino]-4-[(4-amino-6-chloro-1,3,5-triazin-2-yl)amino] phenyl]azo]-1,3,6-Naphthalenetrisulfonic acid, trisodium salt (9CI); also known by Amective Golden Yellow IRX; C.I. 13248; C.I. Reactive Orange 12; Chemictive Golden Yellow RH; Cibacron Golden Yellow 2R; Cibacron Golden Yellow F 2RA; Orbaktiv Yellow T 3RA; Ostazin Golden Yellow H-R; Procion Golden Yellow H-R; Procion Golden Yellow HRS; Procion Yellow H 3R; Procion Yellow P 3R; Reactive Orange 12; Xiron Golden Yellow 2R-HD. For example, FIG. 1S represents a schematic of a N-halamine biocidal molecule modified pursuant to the present invention which is a modification of the molecule identified by CAS number 70616-89-6; 2-[[6-[(4-amino-6-chloro-1,3,5-triazin-2-yl)methylamino]-1-hydroxy-3-sulfo-2-naphthalenyl]azo]-1,5-Naphthalenedisulfonic acid, trisodium salt (9CI); also known by C.I. 18270; C.I. Reactive Orange 13; Chemictive Brilliant Orange 2RH; Cibacron Orange 2R; Cibacron Orange P 2R; Helaktyn Orange D 2R; Ismative Orange SH 2R; Orbaktiv Brilliant Orange T 2R; Ostazin Brilliant Orange H 2R; Procion Brilliant Orange H 2R; Procion Orange H 2R; Procion Orange P 2R; Procion Orange PX 2R; Reactive Orange 13; Xiron Brilliant Orange R-HD.

For example, FIG. 1T represents a schematic of a N-halamine biocidal molecule modified pursuant to the present invention which is a modification of the molecule identified by CAS number 70788-63-5; bis[2-[[6-[(4,6-dichloro-1,3,5-triazin-2-yl)amino]-1-hydroxy-3-sulfo-2-naphthalenyl]azo]benzoato(3-)]-Chromate(3-), disodium hydrogen (9CI); also known by Benzoic acid, 2-[[6-[(4,6-dichloro-1,3,5-triazin-2-yl)amino]-1-hydroxy-3-sulfo-2-naphthalenyl]azo]-, chromium complex; C.I. 179060; C.I. Reactive Brown 10; Mikacion Red Brown 4RS; Orbaktiv Brown M 2G; Procion Brown MX 5BR; Procion Red Brown M 4R; Reactive Brown 10; Sigma Reactive Brown 10. For example, FIG. 1U represents a schematic of a N-halamine biocidal molecule modified pursuant to the present invention which is a modification of the molecule identified by CAS number 70865-31-5; 4-amino-6-[[5-[(4,6-dichloro-1,3,5-triazin-2-yl)amino]-2-sulfophenyl]azo]-3-[(2,5-disulfophenyl) azo]-5-hydroxy-2,7-Naphthalenedisulfonic acid, pentasodium salt (9CI); also known by C.I. 205070; C.I. Reactive Blue 109; Ostazin Blue S 2G; Procion Blue MX 2G; Procion blue MX 2G125; Reactive Blue 109.

For example, FIGS. 1V and 1W illustrate schematics of N-halamine biocidal molecules modified pursuant to the present invention which are modifications of the molecule identified by CAS number 145017-98-7; 5-[[4-chloro-6-[(3-sulfophenyl)amino]-1,3,5-triazin-2-yl]amino]-4-hydroxy-3-[[4-[[2-(sulfooxy) ethyl]sulfonyl]phenyl]azo]-2,7-Naphthalenedisulfonic acid, tetrasodium salt (9CI); also known by C.I. 18221; C.I. Reactive Red 198; Reactive Red 198; Reactive Red RB; Remazol Red RB; Remazol Red RB 133. For example, FIG. 1X represents a schematic of a molecule modified pursuant to the present invention which is a modification of the molecule identified by CAS number 118578-11-3; 5-[[4-chloro-6-[[4-[[4-chloro-6-[[8-hydroxy-3,6-disulfo-7-[(2-sulfophenyl)azo]-1-naphthalenyl]amino]-1,3,5-triazin-2-yl]amino]phenyl]methylamino]-1,3,5-triazin-2-yl] amino]-4-hydroxy-3-[(2-sulfophenyl)azo]-2,7-Naphthalenedisulfonic acid, potassium sodium salt (9CI); also known by C.I. 293755; C.I. Reactive Red 231; Procion Brilliant Red H-EGXL; Procion Red HEGXL; Reactive Red 231.

For example, FIG. 1Y represents a schematic of a N-halamine biocidal molecule modified pursuant to the present invention which is a modification of the molecule identified by CAS number 6471-09-6; 5-[[4-[[4-[[4-[(4-amino-9,10-dihydro-9,10-dioxo-3-sulfo-1-anthracenyl) amino]-2-sulfophenyl]amino]-6-(phenylamino)-1,3,5-triazin-2-yl]amino]phenyl]azo]-2-hydroxy-Benzoic acid, trisodium salt (9CI); also known by Chlorantine Fast Green 5GLL (6CI); C.I. 14155; C.I. Direct Green 28; Chrome Leather Green 5GLL; Coprantine Green 5GLL; Direct Green 28; Durazol Green 5G; Helion Green 5GL; Pyrazol Fast Green 5GL; Saturn Green L 5G; Sirius Green F 4G; Solantine Green 5GLL; Solar Green 5GL; Solius Light Green 3G; Solophenyl Brilliant Green 5GL; Suprexcel Green 5GL; Triantine Light Green GGL.

For example, FIG. 1Z represents a schematic of a N-halamine biocidal molecule modified pursuant to the present invention which is a modification of the molecule identified by CAS number 6388-26-7; 2-hydroxy-5-[[4-[[4-[[8-hydroxy-7-[[4-[(8-hydroxy-3,6-disulfo-1-naphthalenyl) azo]-2-methoxy-5-methylphenyl]azo]-3,6-disulfo-1-naphthalenyl]amino]-6-(phenylamino)-1,3,5-triazin-2-yl]amino] phenyl]azo]-Benzoic acid, pentasodium salt (9CI); also known by C.I. Direct Green 26 (7CI); C.I. Direct Green 26, pentasodium salt (8CI); Chlorantine Fast Green BLL (6CI); Amanil Fast Green BLC; C.I. 34045; Chlorantine Fast Green BBL; Chrome Leather Green BLL; Diazol Light Green BL; Diazol Light Green BMA; Direct Fast Green BL; Direct Green 26; Fabramine Green LB; Fastusol Green LB; Fenaluz Green B; Helion Green BL; Lumison Green BL; Orbantin Green BL; Pontamine Fast Green GL; Pyrazol Fast Green BL; Saturn Green LB; Sirius Green S 4B; Solantine Green BL; Solar Green BL; Solius Light Green BL; Solophenyl Green 155; Solophenyl Green B; Solophenyl Green BL; Solophenyl Green BLE; Solophenyl Green BLE 155%; Tertrodirect Fast Green SBL.

Figure 2:
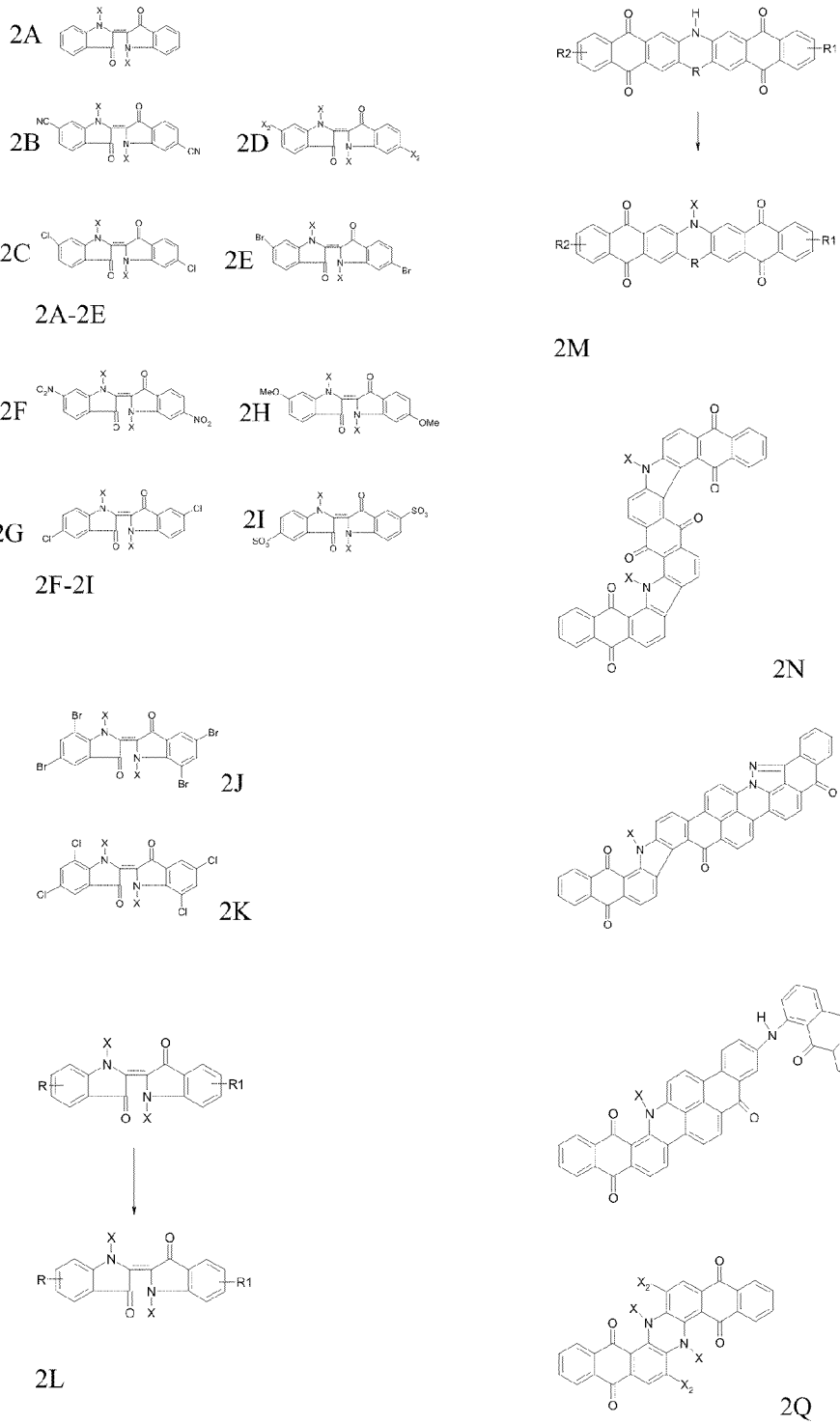
FIG. 2A-2W are images of the structure of colorants-based N-halamine compounds of the present invention.
Figure 2:
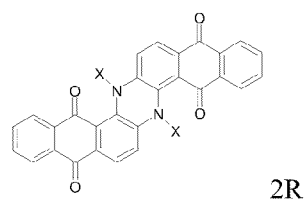
Figure 2:
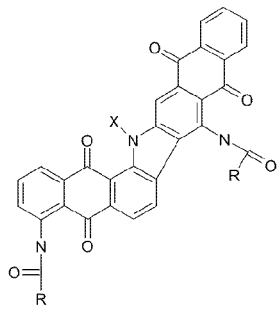
Figure 2:
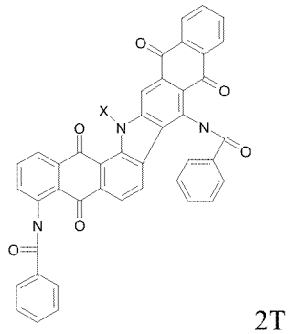
Figure 2:
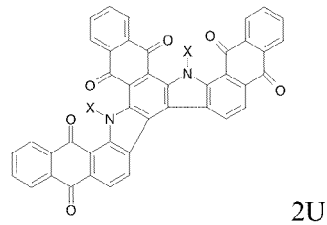
Figure 2:
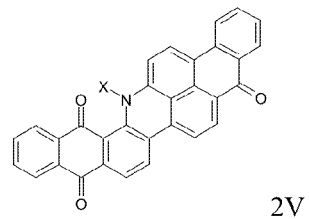
Figure 3:
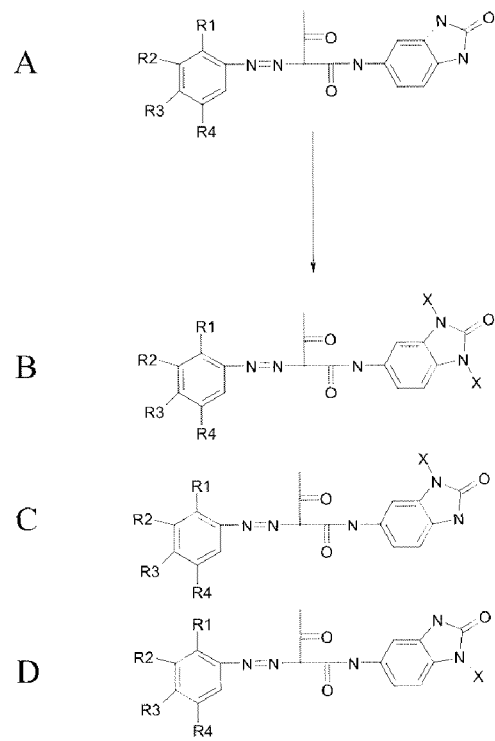
FIGS. 3A-3D is a schematic of a reaction to produce a colorants-based N-halamine compound of the present invention.
Figure 4:
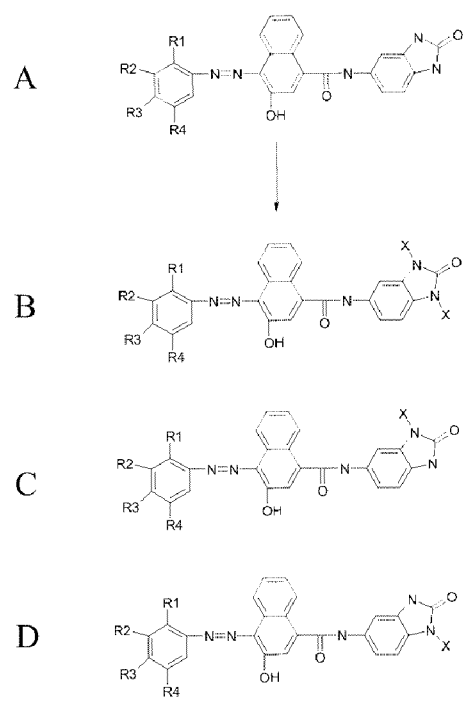
FIGS. 4A-4D is a schematic of another reaction to produce a colorants-based N-halamine compound of the present invention.
Figure 5:
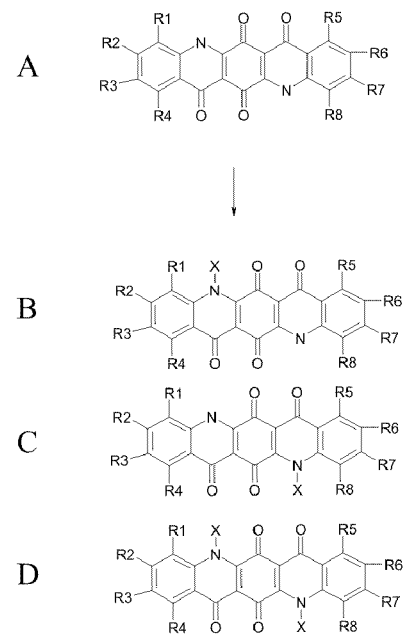
FIGS. 5A-5D is a schematic of another reaction to produce a colorants-based N-halamine compound of the present invention.
Figure 6:
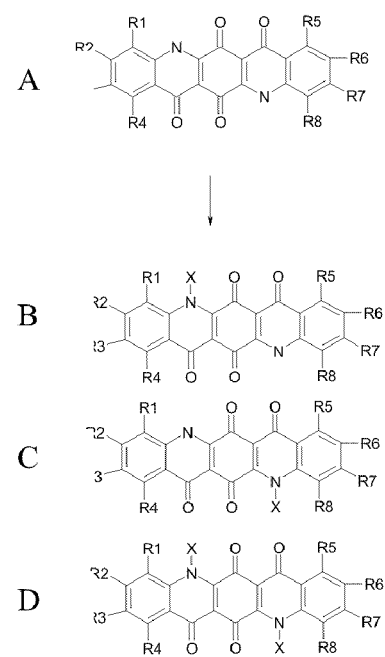
FIGS. 6A-6D is a schematic of another reaction to produce a colorants-based N-halamine compound of the present invention.
Figure 7:
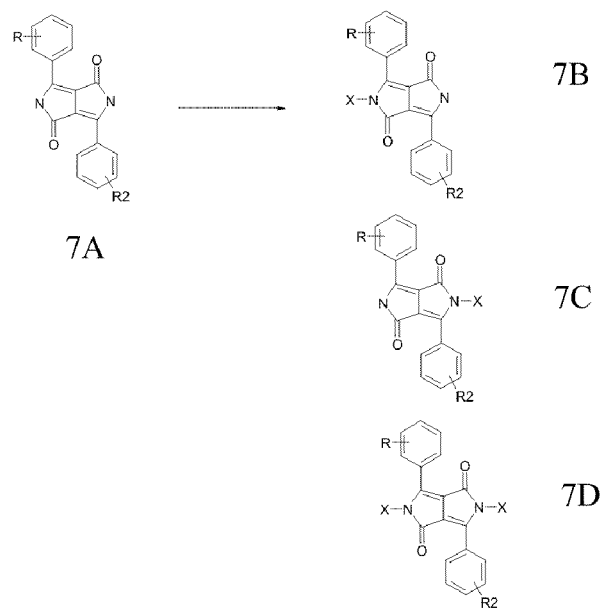
FIGS. 7A-7D is a schematic of another reaction to produce a colorants-based N-halamine compound of the present invention.

For example, FIG. 2A represents a schematic of a N-halamine biocidal molecule modified pursuant to the present invention which is a modification of the molecule identified by CAS number 482-89-3, 2-(1,3-dihydro-3-oxo-2H-indol-2-ylidene)-1,2-dihydro-3H-Indol-3-one (9CI); also known by Indigo Pure BASF (6CI); [Δ2,2'-Biindoline]-3,3'-dione (8CI); Δ2,2'-Bipseudoindoxyl; 11669 Blue; Blue No. 201; C Blue 22; C.I. 73000; C.I. Natural Blue 1; C.I. Pigment Blue 66; C.I. Vat Blue 1; Cystoceva; D and C Blue No. 6; D&C Blue No. 6; D+C Blue No. 6; Diindogen; Indigo; Indigo Blue; Indigo Ciba; Indigo Ciba SL; Indigo J; Indigo N; Indigo NAC; Indigo NACCO; Indigo P; Indigo PLN; Indigo Powder W; Indigo Pure BASF Powder K; Indigo Synthetic; Indigo VS; Indigotin; Indigotin (natural); Indigotine; Japan Blue 201; Lithosol Deep Blue B; Mitsui Indigo Paste; Mitsui Indigo Pure; Mitsui Indigo Pure EXN; Monolite Fast Navy Blue BV; Natural Blue 1; Natural blue indigotin; Pigment Blue 66; Pigment Indigo; Pigment Indigo V; Reduced Dark Blue VB; Synthetic Indigo; Synthetic Indigo TS; Vat Blue 1; Vat Dark Blue VB; Vulcafix Blue R; Vulcafor Blue A; Vulcanosine Dark Blue L; Vulcol Fast Blue GL; Vynamon Blue A; [Δ2,2'(3H,3'H)-Biindole]-3,3'-dione.

For example, FIG. 2B represents a schematic of a N-halamine biocidal molecule modified pursuant to the present invention which is a modification of the molecule identified by CAS number 874304-03-7, 2-(6-cyano-1,3-dihydro-3-oxo-2H-indol-2-ylidene)-2,3-dihydro-3-oxo-1H-Indole-6-carbonitrile (9CI).

For example, FIGS. 2C and 2D illustrate schematics of N-halamine biocidal molecules modified pursuant to the present invention which are modifications of the molecule identified by CAS number 97724-36-2, 6-chloro-2-(6-chloro-1,3-dihydro-3-oxo-2H-indol-2-ylidene)-1,2-dihydro-3H-Indol-3-one (9CI); also known by Indigotin, 6,6'-dichloro-(6CI); [Δ2-2'-Biindoline]-3,3'-dione, 6,6'-dichloro-(7CI); 6,6'-Dichloroindigo.

For example, FIG. 2E represents a schematic of a N-halamine biocidal molecule modified pursuant to the present invention which is a modification of the molecule identified by CAS number 19201-53-7, 6-bromo-2-(6-bromo-1,3-dihydro-3-oxo-2H-indol-2-ylidene)-1,2-dihydro-3H-Indol-3-one (9CI); also known by Indigotin, 6,6'-dibromo-(6CI); [Δ2,2'-Biindoline]-3,3'-dione, 6,6'-dibromo-(7CI,8CI); 6,6'-Dibromoindigo; 6,6'-Dibromoindigotin; C.I. 75800; C.I. Natural Violet 1; Purple of the Ancients; Royal purple; Tyrian Purple.

For example, FIG. 2F represents a schematic of a N-halamine biocidal molecule modified pursuant to the present invention which is a modification of the molecule identified by CAS number 94428-95-2, 2-(1,3-dihydro-6-nitro-3-oxo-2H-indol-2-ylidene)-1,2-dihydro-6-nitro-3H-Indol-3-one (9CI); also known by [Δ2,2'-Biindoline]-3,3'-dione, 6,6'-dinitro-(7CI); 6,6'-Dinitroindigo.

For example, FIG. 2G represents a schematic of a N-halamine biocidal molecule modified pursuant to the present invention which is a modification of the molecule identified by CAS number 6872-04-4, 5-chloro-2-(5-chloro-1,3-dihydro-3-oxo-2H-indol-2-ylidene)-1,2-dihydro-3H-Indol-3-one (9CI); also known by Indigotin, 5,5'-dichloro-(6CI); [Δ2,2'-Biindoline]-3,3'-dione, 5,5'-dichloro- (7CI, 8CI); 5,5'-Dichloroindigo; 5,5'-Dichloroindigotin.

For example, FIG. 2H represents a schematic of one embodiment of a N-halamine biocidal molecule modified pursuant to the present invention is a modification of the molecule identified by CAS number 49764-76-3, 2-(1,3-dihydro-6-methoxy-3-oxo-2H-indol-2-ylidene)-1,2-dihydro-6-methoxy-3H-Indol-3-one (9CI); also known by 6,6'-Dimethoxyindigo.

For example, FIG. 2I represents a schematic of a N-halamine biocidal molecule modified pursuant to the present invention which is a modification of the molecule identified by CAS number 860-22-0, 2-(1,3-dihydro-3-oxo-5-sulfo-2H-indol-2-ylidene)-2,3-dihydro-3-oxo-1H-Indole-5-sulfonic acid, disodium salt (9CI); also known by C.I. Acid Blue 74 (6CI); [Δ2,2'-Biindoline]-5,5'-disulfonic acid, 3,3'-dioxo-, disodium salt (8CI); 12070 Blue; 1311 Blue; 5,5'-Indigodisulfonic acid disodium salt; A.F. Blue No. 2; Acid Blue 74; Acid Blue W; Acid Leather Blue IC; Airedale Blue IN; Amacid Brilliant Blue; Aniline Carmine Powder; Ariavit Indigo Carmine; Atul Indigo Carmine; Bucacid Indigotine B; C.I. 73015; C.I. 75781; C.I. Food Blue 1; C.I. Natural Blue 2; Canacert Indigo Carmine; Carmine Blue; Cilefa Blue R; Disodium 5,5'-indigodisulfonate; Disodium 5,5'-indigotin disulfonate; Dolkwal Indigo Carmine; E 132; Edicol Supra Blue X; FD & C Blue 2; FD and C Blue 2; FD and C Blue No. 2; FD&C Blue No. 2; Food Blue 1; Food Blue 2; Food Blue No. 1; Food Blue No. 2; Grape Blue A; HD Indigo Carmine; HD Indigo Carmine Supra; Hexacert Blue No. 2; Hexacol Indigo Carmine Supra; Indigo Carmine A; Indigo Carmine AC; Indigo Carmine BP; Indigo Carmine Conc. FQ; Indigo Carmine Powder; Indigo Carmine X; Indigo Extract; Indigo carmine; Indigo carmine NB; Indigotin; Indigotin (solubilized); Indigotine; Indigotine B; Indigotine Blue LZ; Indigotine Carmine; Indigotine Extra Pure A; Indigotine I; Indigotine IA; Indigotine Lake; Indigotine N; Indigotine disodium salt; Indocarmine F; Intense Blue; Japan Blue 2; L Blue Z 5010; Maple Indigo Carmine; Mitsui Indigo Carmine; San-ei Indigo Carmine; Sodium 5,5'-indigodisulfonate; Sodium 5,5'-indigotindisulfonate; Soluble indigo; Soluble indigo blue; Sumitomo Wool Blue SBC; Usacert Blue No. 2; Usacert FD and C Blue No. 2; WAS 35.

For example, FIGS. 2J and 2K illustrate schematics of N-halamine biocidal molecules modified pursuant to the present invention which are modifications of the molecule identified by CAS number 2475-31-2, 5,7-dibromo-2-(5,7-dibromo-1,3-dihydro-3-oxo-2H-indol-2-ylidene)-1,2-dihydro-3H-Indol-3-one (9CI); also known by Indigotin, 5,5',7,7'-tetrabromo-(6CI); [Δ2,2'-Biindoline]-3,3'-dione, 5,5',7,7'-tetrabromo-(7CI,8CI); 5,5',7,7'-Tetrabromoindigo; Ahcovat Printing Blue 2BD; Amanthrene Navy Blue 2B-MF; Amanthrene Navy Blue New; Arlanone Blue 2B; BASF Brilliant Indigo 4B; BASF Brilliant Indigo 4B-D; BASF Brilliant Indigo 4BC; Brilliant Indigo 4B; Brilliant Indigo 4B-D; Brilliant Indigo 4BJD; Brilliant Indigo 4BR; Brilliant Indigo 4BV; Bromindigo; Bromindigo 2BD; C.I. 73065; C.I. Vat Blue 5; Ciba Blue 2B; Ciba Blue 2BD; Ciba Blue 2BDG; Ciba Blue 2BN; Ciba Blue 2BPF; Ciba Brilliant Blue BS; Durindone Blue 4B; Durindone Blue 4BC; Durindone Blue 4BCP; Durindone Printing Blue 4BC; Hostavat Blue 2BD; Hostavat Blue 4BR; Indigo 4B; Mitsui Tsuya Indigo 2B; NSC 400980; Solindene Blue 2BD; Sulfanthrene Blue 2B; Tetra Blue 2B; Tetrabromoindigo; Thiovat Brilliant Indigo 4BR; Tina Blue 2B; Tsuya Indigo 2B; Vat Blue 4B; Vat Blue 5.

FIG. 2L is a reaction schematic of the halogenation of an indigo vat dye to form a biocidal indigo vat dye. The structures are general structures with R and $R_1$ being independently an alkyl group, an alkylene group, an alkenyl group, an alkynyl group, an aryl group, an alkoxy group, an alkylcarbonyl group, an alkylcarboxyl group, an amido group, a carboxyl group or a halogen. Furthermore, the R and/or $R_1$ groups may be substituted with one or more alkyl groups, alkylene groups, alkenyl groups, alkynyl groups, aryl groups, alkoxy groups, alkylcarbonyl groups, alkylcarboxyl groups, amido groups, carboxyl groups or halogens and X being independently a halogen.

The present invention also provides dyes having the general structure listed below. The groups A and C are ring structures having between 4 and 8 members fused to the ring B which is a 5 member ring or a six member ring depending on the specific dye. Optionally, one or more of the rings may contain 1-3 heteroatoms. For example, FIGS. 2M-2V illustrate different molecules having this structure.

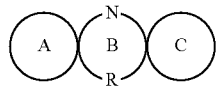

Other example, include rings A and C may be single rings or a multiple fused rings bound to the ring B. In addition, rings A and C may be tethered or connected to ring B through one or more atoms, heteroatoms or rings. The multiple fused rings may vary in number depending on the specific dye being used. In addition, rings A, B, and C may be modified, fused to other rings or substituted.

FIG. 2M is a reaction schematic of the halogenation of ananthraquinon based vat dye to form a N-halamine biocidal ananthraquinon based vat dye. The structures are general structures with R and $R_1$ being independently an alkyl group, an alkylene group, an alkenyl group, an alkynyl group, an aryl group, an alkoxy group, an alkylcarbonyl group, an alkylcarboxyl group, an amido group, a carboxyl group or a halogen. Furthermore the R group may be substituted with one or more alkyl groups, alkylene groups, alkenyl groups, alkynyl groups, aryl groups, alkoxy groups, alkylcarbonyl groups, alkylcarboxyl groups, amido groups, carboxyl groups or halogens and X being independently a halogen.

For example, FIG. 2N represents a schematic of a N-halamine biocidal molecule modified pursuant to the present invention which is a modification of the molecule identified by CAS number 2172-33-0, Dinaphtho[2,3-i:2',3'-i']benzo[1,2-a:4,5-a']dicarbazole-5,7,12,17,19,24(6H,18H)-hexone (7CI,8CI,9CI); also known by Benzo[1,2-i,4,5-i']bisnaphtho[2,3-a]carbazole-5,7,12,17,19,24-hexone, 6,18-dihydro-(5CI); Dinaphtho[2,3-i:2',3'-i']benzo[1,2-a:4,5-a'-]dicarbazole-5,7,12,17,19,24(6H,18H)-(6CI); Benzadone Yellow 3RT; Bis[anthraquinone(2,3-b)pyrrolo][2,3,2',3'-b,b'] anthraquinone; C.I. 70805; C.I. Vat Orange 11; C.I. Vat Orange 11:1; Carbanthrene Yellow 3R; Cibanone Yellow 3R; Cibanone Yellow F 3R; Cibanone Yellow F 3RF; Helanthrene Yellow 3RT; Indanthren Yellow 3R; Indanthren Yellow 3RT; Indanthrene Yellow 3R; Indanthrene Yellow 3RT; Mikethrene Yellow 3RT; Navinon Yellow 3RT; Navinon Yellow 3RTSD; Ostanthren Yellow 3RT; Paradone Yellow 3RT; Pemithrene Yellow 3RT; Ponsol Yellow 3R; Romantrene Yellow F 3RT; Sandothrene Yellow N 3R; Solanthrene Orange BJ; Tinon Yellow 3R-F; Vat Orange 11:1; Vat Yellow 3R.

For example, FIG. 2O represents a schematic of a N-halamine biocidal molecule modified pursuant to the present invention which is a modification of the molecule identified by CAS number 2278-50-4, 1H-Benz[6,7]indazolo [2,3,4-fgh]naphtha[2'',3'':6',7']indolo[3',2':5,6]anthrax[2,1, 9-mna]acridine-2,7,10,15-tetrone (9CI); also known by 5H-Benz[6,7]indazolo[2,3,4-fgh]naphtha[2'',3'':6',7']indolo [3',2':5,6]anthrax[2,1,9-mna]acridine-5,8,13,25(24H)-tetrone (7Cl,8Cl); Benzadone Grey M; C.I. 71000; C.I. Vat Black 8; Caledon Grey M; Indanthren Grey M; Mikethrene Grey M; Mikethrene Grey MG; Nihonthrene Grey M; Ostanthren Grey M; Paradone Grey M; Paradone Grey MG; Vat Black 8; Vat Gray S; Vat Grey M; Vat Grey S.

For example, FIG. 2P represents a schematic of a N-halamine biocidal molecule modified pursuant to the present invention which is a modification of the molecule identified by CAS number 4395-53-3, Anthra[2,1,9-mna] naphth[2,3-h]acridine-5,10,15(16H)-trione, 3-[(9,10-dihydro-9,10-dioxo-1-anthracenyl)amino]-(9CI); also known by Anthra[2,1,9-mna]naphth[2,3-h]acridine-5,10,15(16H)-trione, 3-(1-anthraquinonylamino)-(7CI,8CI); Indanthrene Olive T (6CI); Ahcovat Olive T; Amanthrene Olive S-MF; Amanthrene Olive T; Atic Vat Olive D; Belanthrene Olive T; Benzadone Olive T; C.I. 69525; C.I. Vat Black 25; Calcoloid Olive T; Calcoloid Olive TCC; Calcoloid Olive TL; Calcoloid Olive TRRC; Caledon Olive D; Carbanthrene Olive T; Cibanone Olive FS; Cibanone Olive S; Cibanone Olive SR; Cibanone Olive SRR; Fenanthren Olive T; Fenanthren Olive T 3R; Helanthrene Olive BT; Helanthrene Olive T; Indanthren Olive T; Indanthrene Olive T 3R; Mayvat Olive T; Mikethrene Olive T; Navinon Olive T-U/D; Nihonthrene Olive T; Novatic Olive D; Nyanthrene Olive T; Palanthrene Olive T; Palanthrene Olive TR; Paradone Olive T; Pemithrene Olive T; Ponsol Olive T; Ponsol Olive TR; Romantrene Olive FT; Romantrene Olive T; Sandothrene Olive NT; Solanthrene Olive F-T; Solanthrene Olive T; Tinon Olive S; Tinon Olive SR; Tinon Olive SRR; Tyrian Olive I-T; Vat Black 25; Vat Gray 2Z; Vat Grey 2Z; Vat Olive T.

For example, FIG. 2Q represents a schematic of a N-halamine biocidal molecule modified pursuant to the present invention which is a modification of the molecule identified by CAS number 130-20-1, 7,16-dichloro-6,15-dihydro-5,9,14,18-Anthrazinetetrone (7CI,8CI,9CI); also known by Indanthrene, 7,16-dichloro-(6CI); 3,3'-Dichloroindanthrone; 7,16-Dichloro-6,15-dihydro-5,9,14,18-anthrazinetetrone; 7,16-Dichloroindanthrone; 7:16-Dichloro-6:15-indanthrone; Ahcovat Blue BCF; Alizanthrene Blue RC; Amanthrene Blue BCL; Atic Vat Blue BC; Benzadone Blue RC; Blue K; C.I. 69825; C.I. Pigment Blue 64; C.I. Vat Blue 6; Calcoloid Blue BLC; Calcoloid Blue BLD; Calcoloid Blue BLFD; Calcoloid Blue BLR; Caledon Blue XRC; Carbanthrene Blue BCF; Carbanthrene Blue BCS; Carbanthrene Blue RBCF; Carbanthrene Blue RCS; Cibanone Blue FG; Cibanone Blue FGF; Cibanone Blue FGL; Cibanone Blue GF; D and C Blue No. 9; Dichloroindanthrone; Fenan Blue BCS; Fenanthren Blue BC; Fenanthren Blue BD; Harmone B 79; Helanthrene Blue BC; Indanthren Blue BC; Indanthren Blue BCA; Indanthren Blue BCS; Indanthrene Blue BC; Indanthrene Blue BCF; Indo Blue B-I; Indo Blue WD 279; Indotoner Blue B 79; Intravat Blue GF; Japan Blue 204; Mikethrene Blue BC; Mikethrene Blue BCS; Monolite Fast Blue 2RV; Monolite Fast Blue 2RVSA; NSC 74700; Navinon Blue BC; Navinon Brilliant Blue RCL; Nihonthrene Blue BC; Nihonthrene Brilliant Blue RCL; Novatic Blue BC; Nyanthrene Blue BFP; Ostanthren Blue BCL; Ostanthren Blue BCS; Palanthrene Blue BC; Palanthrene Blue BCA; Paradone Blue RC; Pemithrene Blue BC; Pigment Blue 64; Ponsol Blue BCS; Ponsol Blue BF; Ponsol Blue BFD; Ponsol Blue BFDP; Ponsol Blue BFN; Ponsol Blue BFND; Ponsol Blue BFP; Resinated Indo Blue B 85; Romantrene Blue FBC; Sandothrene Blue NG; Sandothrene Blue NGR; Sandothrene Blue NGW; Solanthrene Blue B; Solanthrene Blue F-SBA; Solanthrene Blue SB; Sumitone Fast Blue 3RS; Tinon Blue GF; Tinon Blue GL; Vat Blue 6; Vat Blue BC; Vat Blue KD; Vat Fast Blue BCS; Vat Green B; Vat Sky Blue K; Vat Sky Blue KD; Vat Sky Blue KP 2F.

For example, FIG. 2R represents a schematic of a N-halamine biocidal molecule modified pursuant to the present invention which is a modification of the molecule identified by CAS number 81-77-6, 6,15-dihydro-5,9,14,18-Anthrazinetetrone (8CI,9CI); also known by Indanthrene (6CI); 6,15-Dihydro-5,9,14,18-anthrazinetetrone; A 3RN; Anthraquinone Deep Blue; Anthraquinone blue; Atic Vat Blue XRN; Benzadone Blue RS; Blue A 3R-K; Blue O; Blue anthraquinone pigment; C.I. 69800; C.I. Food Blue 4; C.I. Pigment Blue 60; C.I. Vat Blue 4; Calcoloid Blue RS; Caledon Blue RN; Caledon Blue XRN; Caledon Brilliant Blue RN; Caledon Paper Blue RN; Caledon Printing Blue RN; Caledon Printing Blue XRN; Carbanthrene Blue 2R; Carbanthrene Blue RS; Carbanthrene Blue RSP; Celliton Blue RN; Cibanone Blue FRS; Cibanone Blue FRSN; Cibanone Blue RS; Cibanone Blue RS-PT 9860; Cibanone Brilliant Blue FR; Cromophtal Blue A 3R; DM Light Blue KT; DM Light Blue KT Crude; Fastogen Super Blue 6070S; Fastogen Super Blue 6075; Fastogen Super Blue 6101; Fenan Blue RSN; Fenanthren Blue RS; Food Blue 4; Fuji AS Blue; Fuji AS Blue 65; Graphtol Blue RL; Helianthrene Blue RS; Heliogen Blue 6470; Heliogen Blue K 6330; Hostaperm Blue RL 01; Indanthren Blue; Indanthren Blue GP; Indanthren Blue GPT; Indanthren Blue IRN; Indanthren Blue RPT; Indanthren Blue RS; Indanthren Blue RSN; Indanthren Blue RSP; Indanthren Brilliant Blue R; Indanthren Printing Blue FRS; Indanthren Printing Blue KRS; Indanthrene Blue; Indanthrene Blue GP; Indanthrene Blue GZ; Indanthrene Blue RP; Indanthrene Blue RS; Indanthrene Blue RSN; Indanthrone; Indanthrone blue; Indanthrone blue (Chinese); Irgazin Blue A 3RN; KET Blue 101; Lake Fast Blue BS; Lake Fast Blue GGS; Latexol Fast Blue SD; Lionogen Blue R; Lutetia Fast Blue RS; Medium Blue; Microlith Blue A 3R-K; Mikethrene Blue RSN; Mikethrene Brilliant Blue R; Monolite Blue 3R; Monolite Fast Blue 3R; Monolite Fast Blue 3RD; Monolite Fast Blue RV; Monolite Fast Blue SRS; N,N'-Dihydro-1,2,1',2'-anthraquinonazine; NSC 47739; NSC 652900; Navinon Blue RSN; Navinon Blue RSN Reddish Special; Nihonthrene Blue RSN; Nihonthrene Brilliant Blue RP; Novatic Blue R; Ostanthren Blue RS; Ostanthren Blue RSN; Ostanthren Blue RSZ; Ostanthrene Blue RS; Palanthrene Blue GPT; Palanthrene Blue GPZ; Palanthrene Blue RPT; Palanthrene Blue RPZ; Palanthrene Blue RSN; Palanthrene Brilliant Blue R; Palanthrene Printing Blue KRS; Paliogen Blue 6470; Paliogen Blue D 6470; Paliogen Blue K 6470; Paliogen Blue L 6385; Paliogen Blue L 6480; Paliogen Blue L 6482; Paliogen Blue L 6495F; Paradone Blue RS; Paradone Brilliant Blue R; Paradone Printing Blue FRS; Pernithrene Blue RS; Pigment Anthraquinone Deep Blue; Pigment Blue 60; Pigment Blue Anthraquinone; Pigment Blue Anthraquinone V; Pigment Deep Blue Anthraquinone; Polymon Blue 3R; Ponsol Blue GZ; Ponsol Blue RCL; Ponsol Blue RPC; Ponsol Brilliant Blue R; Ponsol RP; Reduced Blue RS; Reduced Blue RSN; Reduction Blue RSN; Romanthrene Blue FRS; Romantrene Blue FRS; Romantrene Blue GGSL; Romantrene Blue RSZ; Romantrene Brilliant Blue FR; Romantrene Brilliant Blue R; SPB 10; Sandothrene Blue NRSC; Sandothrene Blue NRSN; Sanyo Threne Blue IRN; Solanthrene Blue RS; Solanthrene Blue RSN; Solanthrene R for Sugar; Sumikacoat Fast Blue BS; Suprapal Blue 2XS5A760; Symuler Fast Blue 6011; Tinon Blue RS; Tinon Blue RSN; Tyrian Blue I-RSN; Tyrian Brilliant Blue I-R; Vat Blue 4; Vat Blue O; Vat Blue OD; Vat Blue RS; Vat Blue RSN; Vat Fast Blue R; Versal Blue GGSL; Vulcafix Fast Blue SD; Vulcafor Fast Blue 3R; Vulcanosine Fast Blue GG; Vulcol Fast Blue S; Vynamon Blue 3R.

For example, FIGS. 2S and 2T illustrate schematics of N-halamine biocidal molecules modified pursuant to the present invention which are modifications of the molecule identified by CAS number 131-92-0, N,N'-(10,15,16,17-tetrahydro-5,10,15,17-tetraoxo-5H-dinaphtho[2,3-a:2',3'-i]carbazole-4,9-diyl)bis-Benzamide (8CI,9CI); also known by 5H-Dinaphtho[2,3-a:2',3'-i]carbazole-5,10,15,17(16H)-tetrone, 4,9-dibenzamido-(7CI); Indanthrene Brown R (6CI); 5H-Dinaphtho[2,3-a:2',3'-i]carbazole, benzamide deriv.; Ahcovat Brown AR; Ahcovat Brown AR-BN; Amanthrene Brown R; Anthragen Brown RA Supra Paste 79-4016; Atic Vat Brown R; Benzadone Brown R; C.I. 69015; C.I. Pigment Brown 28; C.I. Vat Brown 3; Calcoloid Brown R; Calcoloid Brown RK; Calcoloid Brown RNB; Calcoloid Brown RNBC; Caledon Brown R; Caledon Brown R 300; Carbanthrene Brown AR; Carbanthrene Brown ARP; Cibanone Brown FGR; Cibanone Brown GR; Fenalac Brown VRA Supra Paste; Fenanthren Brown D; Fenanthren Brown R; Helio Fast Brown R Presscake 79-4003; Indanthren Brown FFR; Indanthren Brown R; Indanthren Brown R-M; Indanthrene Brown RAP; Indanthrene Brown RARWP; Indanthrene Brown RN; Indanthrene Brown RWP; Leucosol Brown 3RN; Mikethrene Brown R; Navinon Brown RSD; Nihonthrene Brown R; Novatic Brown R; Nyanthrene Brown R; Palanthrene Brown R; Pernithrene Brown R; Ponsol Brown ARD; Ponsol Brown ARN; Romantrene Brown FR; Sandothrene Brown NR; Sandothrene Brown NRF; Solanthrene Brown F-R; Solanthrene Brown R; Tinon Brown GR; Tinon Brown GRF; Tyrian Brown I-FFR; Tyrian Brown I-R; Vat Brown 3; Vat Brown K.

For example, FIG. 2U represents a schematic of a N-halamine biocidal molecule modified pursuant to the present invention which is a modification of the molecule identified by CAS number 2475-33-4, Naphth[2',3':6,7]indolo[2,3-c]dinaphtho[2,3-a:2',3'-i]carbazole-5,10,15,17,22,24-hexone, 16,23-dihydro-(9CI), also known by Dinaphtho [2,3-a:2',3'-i]naphth[2',3':6,7]indolo[2,3-c]carbazole-5,10, 15,17,22,24-hexone, 16,23-dihydro-(6CI,7CI,8CI); Ahcovat Brown BR; Amanthrene Brown BR; Benzadone Brown BR; Brown SK; C.I. 70800; C.I. Vat Brown 1; Calcoloid Brown BR; Caledon Dark Brown 3R; Carbanthrene Brown BR; Chemithrene Brown BR; Cibanone Brown BR; Cibanone Brown FBR; Fenanthren Brown BR; Indanthren Bronze BR; Indanthren Brown BR; Indanthrene Brown BR; Mayvat Brown BR; Mikethrene Brown BR; Nihonthrene Brown BR; Novatic Brown BR; Nyanthrene Brown RB; Ostanthren Brown BR; Palanthrene Brown BR; Paradone Red Brown 2RD; Ponsol Brown RBT; Romantrene Brown FBR; Romantrene Brown FGR; Sandothrene Brown NBR; Solanthrene Brown BR; Solanthrene Brown F-BR; Solanthrene Brown JR; Tinon Brown BR; Tyrian Brown I-BR; Vat Brown 1; Vat Brown BR; Vat Brown SK; Vat Brown SKD.

For example, FIG. 2V represents a schematic of a N-halamine biocidal molecule modified pursuant to the present invention which is a modification of the molecule identified by CAS number 3271-76-9, Anthra[2,1,9-mna]naphth[2,3-h]acridine-5,10,15(16H)-trione (6CI,7CI,8CI, 9CI); also known by Ahcovat Olive Green BL; Ahcovat Olive Green BL-F; Ahcovat Olive Green BLD; Ahcovat Printing Olive Green BL; Amanthrene Olive Green B; Amanthrene Supra Olive Green B; Arlanthrene Olive Green B; Atic Vat Olive Green B; Belanthrene Olive Green B; Benzadone Olive Green B; C.I. 69500; C.I. 70311; C.I. Vat Green 3; Calcoloid Olive Green BD; Calcoloid Olive Green BDC; Calcoloid Olive Green BDL; Calcoloid Olive Green BN; Calcoloid Olive Green BNC; Caledon Olive Green B; Caledon Printing Olive Green B; Carbanthrene Olive Green B; Cibanone Olive 2B; Cibanone Olive 2BD; Cibanone Olive B; Cibanone Olive FB; Fenanthren Olive Green B; Helanthrene Olive Green B; Indanthren Olive Green B; Indanthrene Olive Green B; Indanthrene Olive Green BA; Mayvat Olive Green B; Mikethrene Olive Green B; Nihonthrene Olive Green B; Nihonthrene Olive Green B Disperse Powder; Novatic Olive Green B; Nyanthrene Olive Green B; Ostanthren Olive Green B; Palanthrene Olive Green B; Pernithrene Olive Green B; Ponsol Green 2BL; Ponsol Green 2BLD; Romantrene Olive Green FB; Sandothrene Olive N 2B; Solanthrene Dark Green F-J; Solanthrene Dark Green J; Tinon Olive B; Tinon Olive BM; Tyrian Olive Green I-B; Vat Green 3; Vat Olive Green B.

FIGS. 3A-3D and 4A-4D are reaction schematics of the halogenation of benzimidazolone Pigments to form N-halamine biocidal benzimidazolone pigments. The structures are general structures with R to $R_4$ being independently an alkyl group, an alkylene group, an alkenyl group, an alkynyl group, an aryl group, an alkoxy group, an alkylcarbonyl group, an alkylcarboxyl group, an amido group, a carboxyl group or a halogen. Furthermore, the R to $R_4$ groups may independently be substituted with one or more alkyl groups, alkylene groups, alkenyl groups, alkynyl groups, aryl groups, alkoxy groups, alkylcarbonyl groups, alkylcarboxyl groups, amido groups, carboxyl groups or halogens and X being independently a halogen. The present invention may be used to convert Benzimidazolone Pigments into N-halamine biocidal dye compound. For example, Pigment yellow 120 (CAS 29920-31-8); Pigment yellow 150 (CAS 61036-28-0); Pigment yellow 154 (CAS 63661-02-9); Pigment yellow 175 (CAS 35636-63-6); Pigment yellow 180 (CAS 77804-81-0); Pigment yellow 181 (CAS 74441-05-7); Pigment yellow 194 (CAS 82199-12-0); Pigment orange 36 (CAS 12236-62-3); Pigment orange 62 (CAS 75601-68-2); Pigment red 171 (CAS 6985-95-1); Pigment red 175 (CAS 6985-92-8); Pigment red 176 (CAS 12225-06-8); Pigment red 185 (CAS 61951-98-2); Pigment red 208 (CAS 31778-10-6); Pigment violet 32 (CAS 12225-08-0); and Pigment brown 25 (CAS 6992.11.6) may be convert into the corresponding N-halamine biocidal pigment compounds.

FIGS. 5A-5D and 6A-6D are reaction schematics of the halogenation of Quinacridone Pigment to form a biocidal Quinacridone Pigment. The structures are general structures with R to $R_4$ being independently an alkyl group, an alkylene group, an alkenyl group, an alkynyl group, an aryl group, an alkoxy group, an alkylcarbonyl group, an alkylcarboxyl group, an amido group, a carboxyl group or a halogen. Further more the R group may be substituted with one or more alkyl groups, alkylene groups, alkenyl groups, alkynyl groups, aryl groups, alkoxy groups, alkylcarbonyl groups, alkylcarboxyl groups, amido groups, carboxyl groups or halogens; and X being independently a halogen.

The present invention may be used to convert Quinacridone Pigments into N-halamine biocidal dye compound. For example, the pigment violet 19 (CAS 1047-16-1); Pigment red 122 (CAS 980-26-7); Pigment red 202 (CAS 68859-50-7); Pigment red 207 (CAS 1047-16-1+CAS 3089-16-5); Pigment red 209 (CAS 3089-17-6); and Pigment orange 48 (CAS 1047-16-1+CAS 1503-48-6) may be convert into the corresponding N-halamine biocidal pigment compounds.

FIGS. 7A-7D are reaction schematics of the halogenation of a diketopyrrole-pyrrolo Pigment to form a biocidal diketopyrrole-pyrrolo Pigment. The structures are illustrated in FIGS. 7A-7D with R to R4 being independently an alkyl group, an alkylene group, an alkenyl group, an alkynyl group, an aryl group, an alkoxy group, an alkylcarbonyl group, an alkylcarboxyl group, an amido group, a carboxyl group or a halogen. Further more the R group may be substituted with one or more alkyl groups, alkylene groups, alkenyl groups, alkynyl groups, aryl groups, alkoxy groups, alkylcarbonyl groups, alkylcarboxyl groups, amido groups, carboxyl groups or halogens and X being independently a halogen.

The present invention may be used to convert diketopyrrole-pyrrolo Pigments into N-halamine biocidal dye compound. For example, Pigment red 254 (CAS 122390-98-1); Pigment red 255 (CAS 120500-90-5); Pigment red 264 (CAS #: N/A); Pigment red 272 (CAS #: N/A); Pigment orange 71 (CAS #: N/A); and Pigment orange 73 (CAS #: N/A) may be convert into the corresponding N-halamine biocidal pigment compounds.

Figure 8:
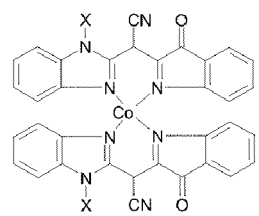
FIG. 8 is an image of the structure of a colorants-based N-halamine compound of the present invention.
Figure 9:
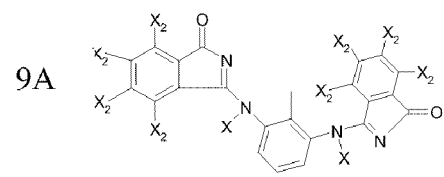
FIGS. 9A-9B are images of the structure of colorants-based N-halamine compounds of the present invention.
Figure 9:
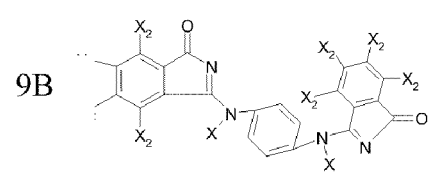
Figure 10:
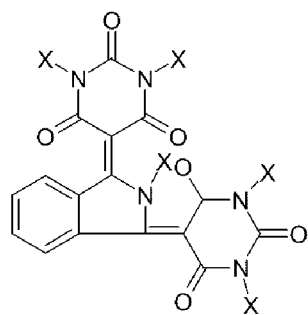
FIG. 10 is an image of the structure of a colorants-based N-halamine compound of the present invention.
Figure 11:
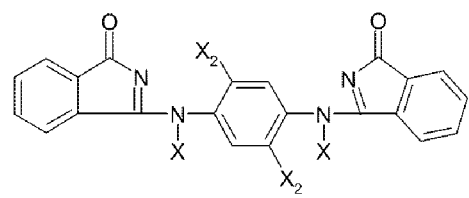
FIG. 11 is an image of the structure of a colorants-based N-halamine compound of the present invention.

The present invention may be used to convert a Pigment (e.g., yellow 177 (CAS 60109-88-8)) into the corresponding N-halamine biocidal dye compound, as seen in FIG. 8. Similarly, the present invention may be used to convert the Pigment orange 68 (CAS 42844-93-9) into the corresponding N-halamine biocidal dye compound. The present invention may be used to convert a Pigment (e.g., yellow 109 (CAS 12769-01-6) or yellow 110 (CAS 5590-18-1)) into the corresponding N-halamine biocidal dye compound as seen in FIGS. 9A and 9B. The present invention may be used to convert a Pigment (e.g., yellow 139 (CAS 36888-99-0)) into the corresponding N-halamine biocidal dye compound as seen in FIG. 10. The present invention may be used to convert a Pigment (e.g., yellow 173 (CAS 51016-63-8)) into the corresponding N-halamine biocidal pigment compound as seen in FIG. 11.

Figure 12:
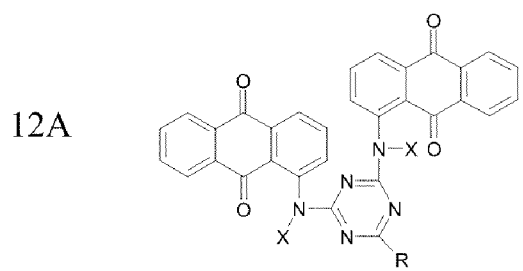
FIG. 12 is an image of the structure of a colorants-based N-halamine compound of the present invention.
Figure 12:
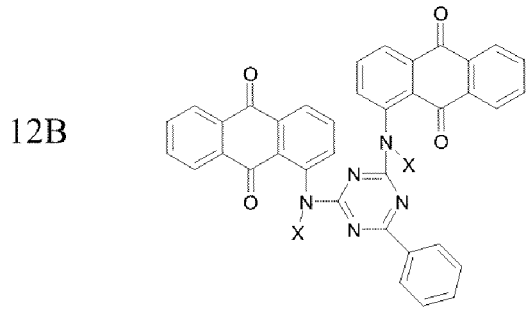
Figure 13:
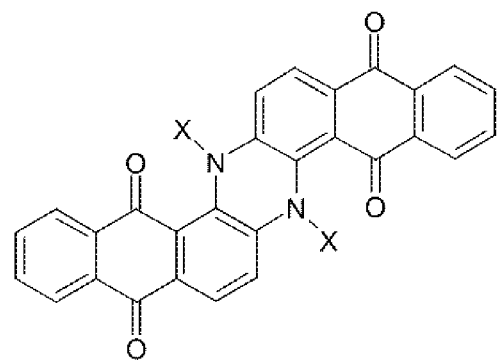
FIG. 13 is an image of the structure of a colorants-based N-halamine compound of the present invention.
Figure 14:
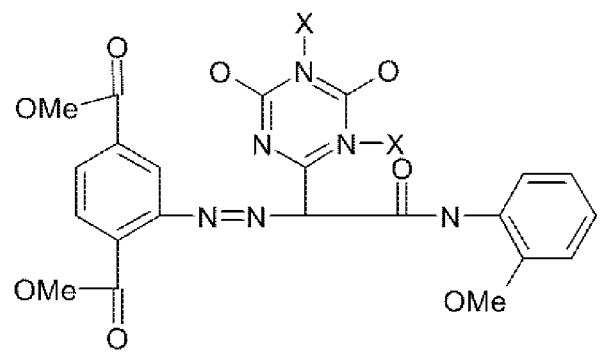
FIG. 14 is an image of the structure of a colorants-based N-halamine compound of the present invention.
Figure 15:
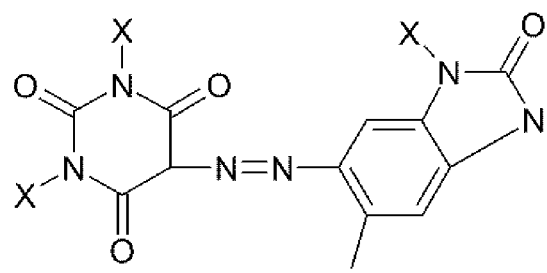
FIG. 15 is an image of the structure of a colorants-based N-halamine compound of the present invention.
Figure 16:
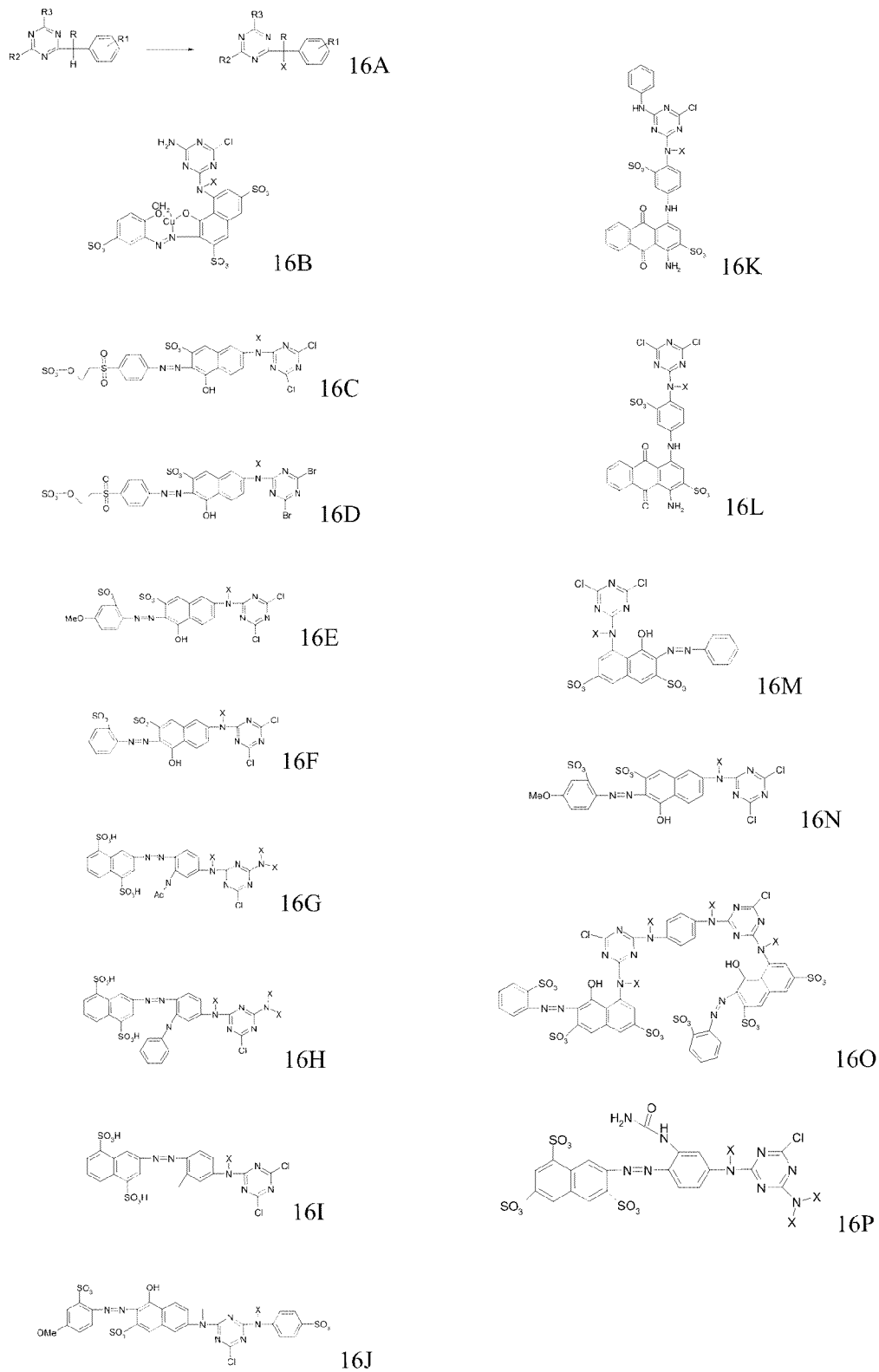
FIG. 16A is a schematic of another reaction to produce a colorants-based N-halamine compound of the present invention.
FIGS. 16B-16DD are images of the structure of colorants-based N-halamine compounds of the present invention.
Figure 16:
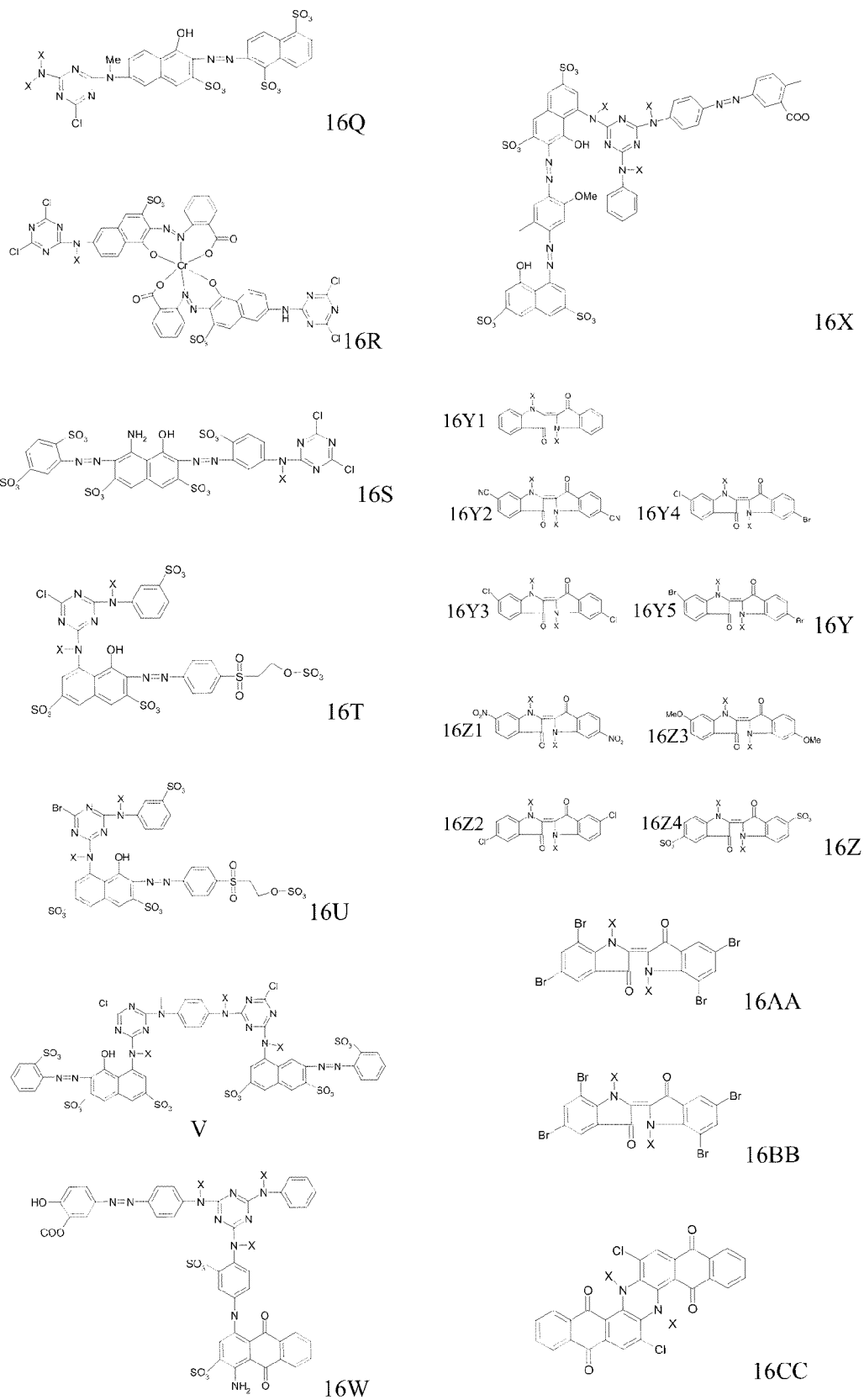
Figure 16:
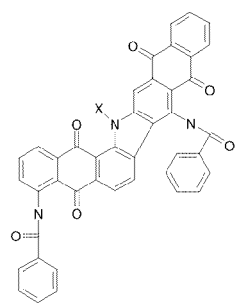

The present invention may be used to convert a pigment (e.g., 147 (CAS 76168-75-7)) into the corresponding N-halamine biocidal pigment compound as seen in FIGS. 12A and 12B. The present invention may be used to convert a Pigment (e.g., blue 60 (CAS 81-77-6)) into the corresponding N-halamine biocidal pigment compound as seen in FIG. 13. The present invention may be used to convert a Pigment (e.g., yellow 182 (CAS 67906-31-4)) into the corresponding N-halamine biocidal pigment compound as seen in FIG. 14. The present invention may be used to convert a Pigment (e.g., orange 64 (CAS 72102-84-2)) into the corresponding N-halamine biocidal pigment compound as seen in FIG. 15.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A biocidal N-halamine dye composition having the formula:

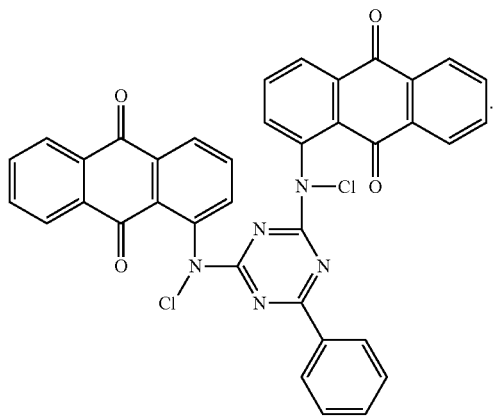 [SMILES: O=C1c2ccccc2C(=O)c2c1cccc2N(Cl)c1nc(-c2ccccc2)nc(N(Cl)c2cccc3c2C(=O)c2ccccc2C3=O)n1]

2. The composition of claim 1, wherein the biocidal N-halamine dye composition is integrated into a bead, a film, a tube, a sheet, a thread, a suture, a gauze, a bandage, an adhesive bandage, a vessel, a container, a cistern, a filter, a membrane, a coating, a paint, a solution, a polymer or combinations thereof.

3. A biofilm resistant surface comprising a surface; and an N-halamine biocidal compound immobilized to the surface to form a biofilm resistant surface, wherein the N-halamine biocidal compound has the formula:

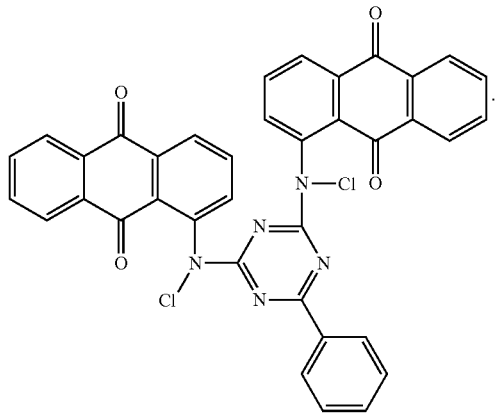 [SMILES: O=C1c2ccccc2C(=O)c2c1cccc2N(Cl)c1nc(-c2ccccc2)nc(N(Cl)c2cccc3c2C(=O)c2ccccc2C3=O)n1]

4. The biofilm resistant surface of claim 3, wherein the surface comprises at least a portion of a fabric, a cloth, a material, a garment, synthetic fabric or a polymer.

5. The biofilm resistant surface of claim 3, wherein the N-halamine biocidal compounds is integrated into a bead, a film, a tube, a sheet, a thread, a suture, a guaze, a bandage, an adhesive bandage, a vessel, a container, a cistern, a filter, a membrane, a coating, a paint, a solution, a polymer or combinations thereof.

6. A biocidal N-halamine dye composition comprising a compound of the formula:

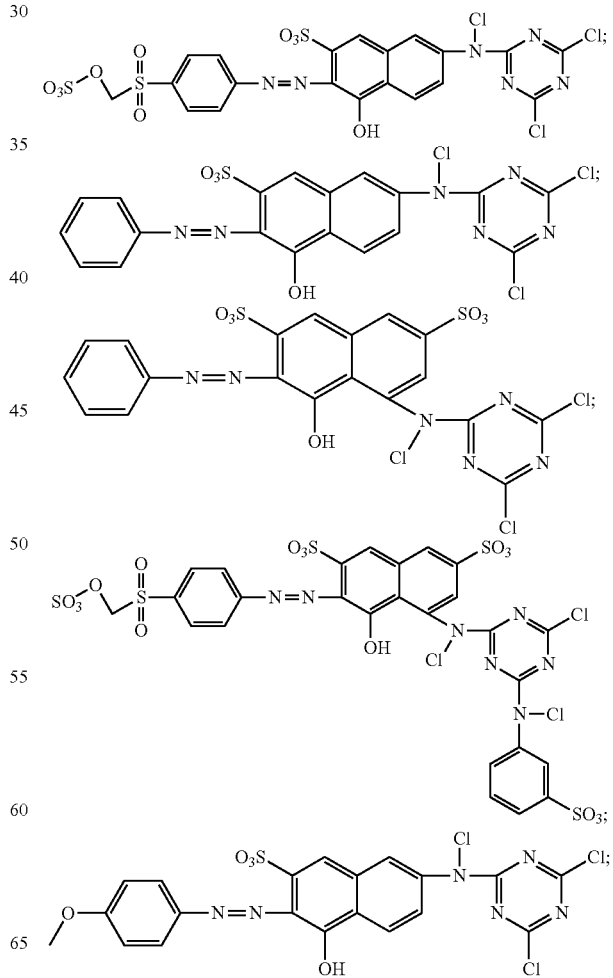

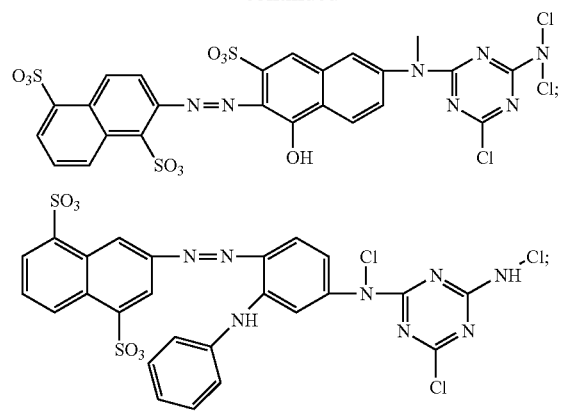
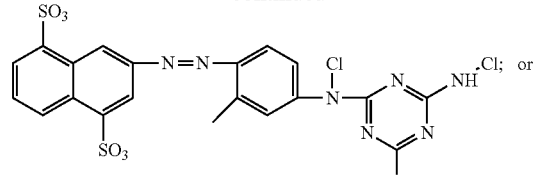
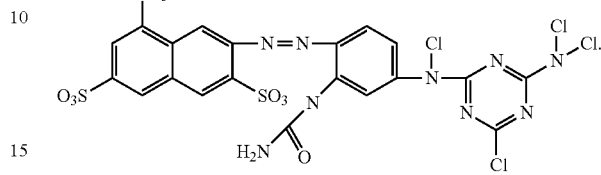
* * * * *